(12) United States Patent
Takaku

(10) Patent No.: US 7,270,857 B2
(45) Date of Patent: Sep. 18, 2007

(54) LIQUID CRYSTAL COMPOSITION AND LIQUID CRYSTAL ELEMENT

(75) Inventor: Koji Takaku, Kanagawa (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 295 days.

(21) Appl. No.: 10/947,364

(22) Filed: Sep. 23, 2004

(65) Prior Publication Data

US 2005/0072962 A1     Apr. 7, 2005

(30) Foreign Application Priority Data

Sep. 26, 2003   (JP)   ............... 2003-334794
Feb. 25, 2004   (JP)   ............... 2004-050265

(51) Int. Cl.
*C09K 19/60*   (2006.01)
*C07D 265/38*  (2006.01)

(52) U.S. Cl. ............... 428/1.1; 428/1.31; 252/299.1; 544/102; 544/104

(58) Field of Classification Search ........... 252/299.01, 252/299.1; 428/1.1, 1.31; 544/102, 104
See application file for complete search history.

(56) References Cited

U.S. PATENT DOCUMENTS 3,731,222 A     5/1973  Drexhage
5,667,719 A *   9/1997  Mortazavi et al. ..... 252/299.01
5,723,065 A *   3/1998  Inaba et al. ............. 252/299.01
5,738,803 A *   4/1998  Shepherd et al. ........ 252/299.1
5,753,145 A *   5/1998  Teng et al. .................. 252/585
5,863,622 A *   1/1999  Jester ........................ 428/1.31

OTHER PUBLICATIONS

CAPLUS 1998: 398382.*
CAPLUS 1986: 26737.*

* cited by examiner

*Primary Examiner*—Shean C Wu
(74) *Attorney, Agent, or Firm*—Buchanan Ingersoll & Rooney PC

(57) ABSTRACT

The present invention relates to a liquid crystal composition comprising a compound represented by the following formula (1) and a liquid crystal and a liquid crystal element containing the liquid crystal composition:

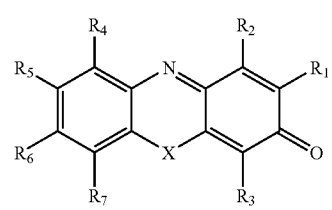

Formula (1)

wherein $R_1$, $R_2$, $R_3$, $R_4$, $R_5$, $R_6$ and $R_7$ each independently represent a hydrogen atom or a substituent; and X represents an oxygen atom or a sulfur atom.

13 Claims, No Drawings

LIQUID CRYSTAL COMPOSITION AND LIQUID CRYSTAL ELEMENT

CROSS-REFERENCE TO RELATED APPLICATIONS

This application claims priority under 35 USC 119 from Japanese Patent Applications, Nos. 2003-334794 and 2004-50265 the disclosure of which are incorporated by reference herein.

BACKGROUND OF THE INVENTION

1. Field of the Invention

The present invention relates to a liquid crystal composition and to a liquid crystal element having a liquid crystal layer containing the liquid crystal composition, and, particularly, to a liquid crystal element which can be preferably used for a guest-host system liquid crystal element.

2. Description of the Related Art

With regard to liquid crystal elements (liquid crystal display elements), many systems have been already proposed. Guest-host system liquid crystal elements enable bright display and are therefore expected to provide liquid crystal elements suitable to a reflection type. In the guest-host system liquid crystal elements, a dichroic dye is dissolved in a liquid crystal, and a light absorption state of the element is made to change based on a change in the orientation of the dichroic dye in accordance with the movement of the liquid crystal in response to an electric field, in order to display an image.

There are descriptions regarding the guest-host system in, for example, B. Bahadur, Handbook of Liquid Crystals, edited by D. Demus, J. Goodby, G. W. Gray, H. W. Spiess and V. Vill, vol. 2A, Willey-VCH, (1998), chapters 3 and 4, pages 257 to 302. It is required that the dichroic dye used for a guest-host system liquid crystal element have proper absorbing characteristics, high-order parameters, high solubility in a host liquid crystal, durability and the like.

As the dichroic dye, for example, an anthraquinone dye has been widely studied, and this dye is disclosed in, for instance, A. V. Ivashchenko, Dichroic Dyes for Liquid Crystal Display, CRC, 1994. However, many anthraquinone dyes have a low absorption coefficient and low solubility in a host liquid crystal, and earnest studies have been made by many researchers to improve the drawbacks of the anthraquinone dyes. Results of these studies are described in, for example, Jpn. J. Appl. Phys. vol. 37., page 3422 (1998).

In the meantime, phenoxazine dyes have a high absorption coefficient and a sharp hue and have therefore been widely studied as fluorescent dyes. Phenoxazine dyes as laser dyes are disclosed in the specification of U.S. Pat. No. 3,731,222. However, it is nowhere suggested that the phenoxazine dyes are used for liquid crystal compositions and liquid crystal elements.

SUMMARY OF THE INVENTION

The present invention has been made in view of the above circumstances. An embodiment of the present invention can provide a dye compound having a high absorption coefficient, a sharp hue, a high order parameter and high solubility. And an embodiment can provide a liquid crystal composition containing the dye compound, and provide a liquid crystal element with a liquid crystal layer containing the liquid crystal composition, the element having high contrast and high absorbing coefficient.

The present inventors have made earnest studies and, as a result, found that a dye compound of the present invention has a high absorption coefficient, a sharp hue, a high order parameter and high solubility. Specifically, a liquid crystal composition and a liquid crystal element of the present invention are as follows.

A first aspect of the present invention provides to a liquid crystal composition comprising a compound represented by the following formula (1) and a liquid crystal:

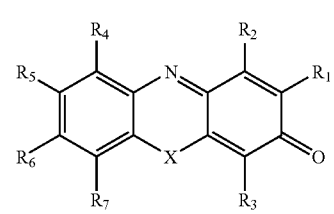

Formula (1)

wherein $R_1$, $R_2$, $R_3$, $R_4$, $R_5$, $R_6$ and $R_7$ each independently represent a hydrogen atom or a substituent; and X represents an oxygen atom or a sulfur atom.

A second aspect of the present invention provides to a liquid crystal element comprising a pair of electrodes at least one of which is a transparent electrode and a liquid crystal layer disposed between the pair of electrodes wherein the liquid crystal layer contains the liquid crystal composition comprising a compound represented by the following formula (1) and a liquid crystal:

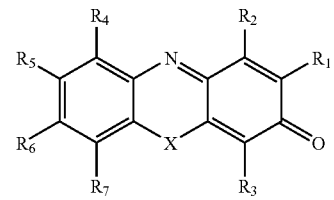

Formula (1)

wherein $R_1$, $R_2$, $R_3$, $R_4$, $R_5$, $R_6$ and $R_7$ each independently represent a hydrogen atom or a substituent; and X represents an oxygen atom or a sulfur atom.

A third aspect of the present invention relates to a compound represented by the following formula (4):

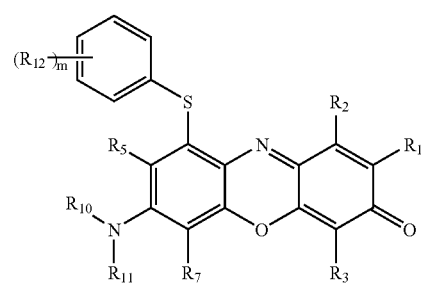

Formula (4)

wherein $R_1$, $R_2$, $R_3$, $R_5$ and $R_7$ each independently represent a hydrogen atom or a substituent; $R_{10}$ and $R_{11}$ each independently represent a hydrogen atom, an alkyl group or an aryl group; $R_{12}$ represents a substituent; and m denotes an integer from 0 to 5.

The fourth aspect of the present invention provides to a liquid crystal composition comprising the compound represented by the following formula (4):

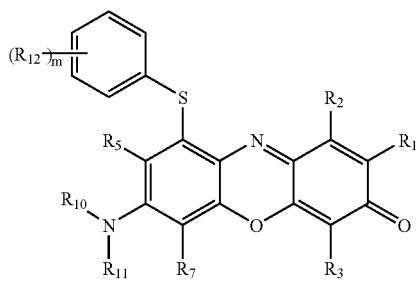

Formula (4)

wherein $R_1$, $R_2$, $R_3$, $R_5$ and $R_7$ each independently represent a hydrogen atom or a substituent; $R_{10}$ and $R_{11}$ each independently represent a hydrogen atom, an alkyl group or an aryl group; $R_{12}$ represents a substituent; and m denotes an integer from 0 to 5.

The fifth aspect of the present invention provides to a liquid crystal element comprising a pair of electrodes at least one of which is a transparent electrode and a liquid crystal layer disposed between the pair of electrodes, wherein the liquid crystal layer contains the liquid crystal composition comprising a compound represented by the following formula (4):

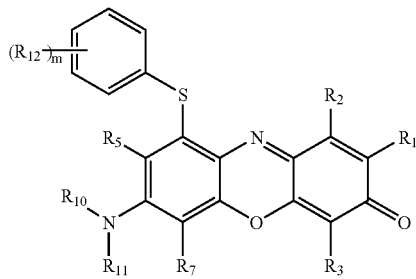

Formula (4)

wherein $R_1$, $R_2$, $R_3$, $R_5$ and $R_7$ each independently represent a hydrogen atom or a substituent; $R_{10}$ and $R_{11}$ each independently represent a hydrogen atom, an alkyl group or an aryl group; $R_{12}$ represents a substituent; and m denotes an integer from 0 to 5.

DETAILED DESCRIPTION OF THE INVENTION

In the present invention, the liquid crystal composition each in the first to the fifth aspect has a high absorption coefficient (high solubility) and exhibits a sharp hue and also the liquid crystal element using the liquid crystal composition shows a high order parameter.

Moreover, a sixth aspect to a eleventh aspect will be explained as the aspects of the present invention.

The sixth aspect of the present invention provides to a liquid crystal composition of the first aspect, wherein the compound represented by the formula (1) is a compound represented by the following formula (2):

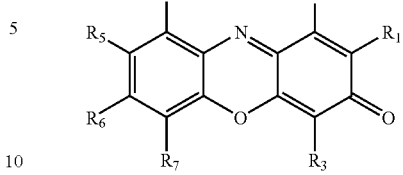

Formula (2)

wherein $R_1$, $R_2$, $R_3$, $R_4$, $R_5$, $R_6$ and $R_7$ each independently represent a hydrogen atom or a substituent.

The seventh aspect of the present invention provides to a liquid crystal composition of the sixth aspect, wherein in the compound represented by the formula (2), $R_1$ is a halogen atom, a carbamoyl group, an acylamino group, an acyl group, an aryloxycarbonyl group or an alkoxycarbonyl group; and $R_6$ is an amino group (which may be an alkylamino group or an arylamino group), a hydroxyl group, a mercapto group, an alkylthio group, an arylthio group, an alkoxy group or an aryloxy group.

The eighth aspect of the present invention provides to a liquid crystal composition of the sixth aspect, wherein the compound represented by the formula (2) has a substituent represented by the following formula (3):

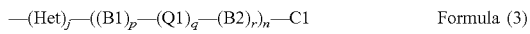

—(Het)$_j$—((B1)$_p$—(Q1)$_q$—(B2)$_r$)$_n$—C1    Formula (3)

wherein Het represents an oxygen atom or a sulfur atom; B1 and B2 each independently represent a divalentaryl group, a heteroaryl group or a cyclic aliphatic hydrocarbon group; Q1 represents a divalent connecting group; C1 represents an alkyl group, a cycloalkyl group, an alkoxy group, an alkoxycarbonyl group or an acyloxy group, j denotes 0 or 1; p, q and r each independently denote a integer from 0 to 5; and n denotes a integer from 1 to 3, provided that (p+r)×n is a number of 3 or more and 10 or less.

The ninth aspect of the present invention provides to a liquid crystal element of the second aspect, wherein the compound contained in the liquid crystal composition and represented by the formula (1) is a compound represented by the following formula (2):

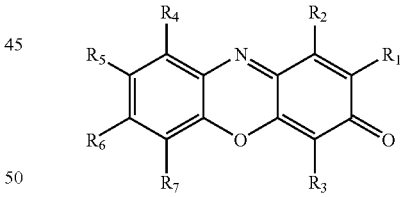

Formula (2)

wherein $R_1$, $R_2$, $R_3$, $R_4$, $R_5$, $R_6$ and $R_7$ each independently represent a hydrogen atom or a substituent.

The tenth aspect of the present invention provides to a liquid crystal element of the ninth aspect, wherein in the compound represented by the formula (2), $R_1$ is a halogen atom, a carbamoyl group, an acylamino group; an acyl group, an aryloxycarbonyl group or an alkoxycarbonyl group and $R_6$ is an amino group (which may be an alkylamino group or an arylamino group), a hydroxyl group, a mercapto group, an alkylthio group, an arylthio group, an alkoxy group or an aryloxy group.

The eleventh aspect of the present invention provides to a liquid crystal element of the ninth aspect, wherein the compound represented by the formula (2) has a substituent represented by the following formula (3):

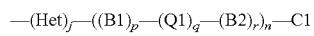
—(Het)$_j$—((B1)$_p$—(Q1)$_q$—(B2)$_r$)$_n$—C1                    Formula (3)

wherein Het represents an oxygen atom or a sulfur atom; B1 and B2 each independently represent a divalent aryl group, a heteroaryl group or a cyclic aliphatic hydrocarbon group; Q1 represents a divalent connecting group; C1 represents an alkyl group, a cycloalkyl group, an alkoxy group, an alkoxycarbonyl group or an acyloxy group; j denotes 0 or 1; p, q and r each independently denote an integer from 0 to 5; and n denotes an integer from 1 to 3, provided that (p+r)×n is a number of 3 or more and 10 or less.

Here, it is disclosed in U.S. Pat. No. 3,731,222 and the like that phenoxazine dyes may be used as laser dyes. However, it is nowhere suggested that this dye is used as a liquid crystal composition or a liquid crystal element.

The dichroism of a dye is specified by the ratio of two colors (R) and the magnitude of the order parameter (S). R and S are also greatly affected by the solubility of the dye in a liquid crystal. Therefore, it cannot be determined only by the performance of a dye for dye use whether the dye is excellent as a GH liquid crystal dye or not and it is always necessary to consider the relation between the dye and the liquid crystal. In particular, dichroic dyes which are usually used are anthraquinone type dyes, azo type dyes and azomethine type dyes which are quite different from phenoxazine dyes in skeleton.

As a result of earnest studies, the inventors of the present invention have found that phenoxazone dyes (phenoxazine-3-one) and phenothiazone dyes (phenothiazine-3-one) are highly soluble in liquid crystals, have a high absorption coefficient and exhibit a sharp hue.

The compound represented by the formula (1) (which has the same meaning as the compound according to the present invention or the dye according to the present invention) will be hereinafter explained in detail.

The liquid crystal composition of the present invention comprises a compound represented by the following formula (1) and a liquid crystal:

Formula (1)

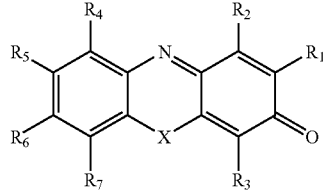

wherein $R_1$, $R_2$, $R_3$, $R_4$, $R_5$, $R_6$ and $R_7$ each independently represent a hydrogen atom or a substituent and X represents an oxygen atom or a sulfur atom.

Among compounds represented by the formula (1), compounds represented by the formula (1) in which X is an oxygen atom, namely compounds represented by the following formula (2) are preferable.

Formula (2)

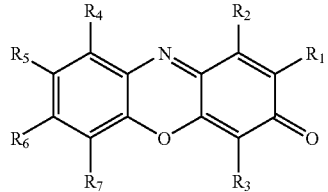

Also, the compounds represented by the formula (1) preferably have a substituent represented by the formula (3).

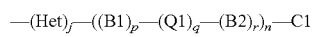
—(Het)$_j$—((B1)$_p$—(Q1)$_q$—(B2)$_r$)$_n$—C1                    Formula (3)

wherein Het represents an oxygen atom or a sulfur atom, B1 and B2 each independently represent a divalent aryl group, a heteroaryl group or a cyclic aliphatic hydrocarbon group, Q1 represents a divalent connecting group, C1 represents an alkyl group, a cycloalkyl group, an alkoxy group, an alkoxycarbonyl group or an acyloxy group, j denotes a number 0 or 1, p, q and r each independently denote an integer from 0 to 5; and n denotes an integer from 1 to 3, provided that (p+r)×n is an integer of 3 or more and 10 or less.

In the formulae (1) and (2), $R_1$, $R_2$, $R_3$, $R_4$, $R_5$, $R_6$ and $R_7$ each independently represent a hydrogen atom or a substituent and $R_{12}$ represents a substituent. $R_1$ and $R_2$, $R_4$ and $R_5$, $R_5$ and $R_6$ and $R_6$ and $R_7$ are respectively combined with each other to make a ring.

Examples of the substituent of each of $R_1$ to $R_7$ and $R_{12}$ include the following substituent group R.

(Substituent Group R)

Examples of the substituent include a halogen atom, alkyl group (including a cycloalkyl group), alkenyl group (including a cycloalkenyl group), alkinyl group, aryl group, heterocyclic group, cyano group, hydroxyl group, nitro group, carboxyl group, alkoxy group, aryloxy group, silyloxy group, heterocyclic oxy group, acyloxy group, carbamoyloxy group, alkoxycarbonyloxy group, aryloxycarbonyloxy group, amino group (including an anilino group), acylamino group, aminocarbonylamino group, alkoxycarbonylamino group, aryloxycarbonylamino group, sulfamoylamino group, alkyl or arylsulfonylamino group, mercapto group, alkylthio group, arylthio group, heterocyclic thio group, sulfamoyl group, sulfo group, alkyl or arylsulfinyl group, alkyl or arylsulfonyl group, acyl group, aryloxycarbonyl group, alkoxycarbonyl group, carbamoyl group, aryl or heterocyclic azo group, imide group, phosphino group, phosphinyl group, phosphinyloxy group, phosphinylamino group and silyl group.

To state in more detail, examples of the halogen atom include a chlorine atom, bromine atom and iodine atom.

Preferable examples of the alkyl group include alkyl groups having 1 to 30 carbon atoms, for example, methyl, ethyl, n-propyl, isopropyl, t-butyl, n-octyl, eicosyl, 2-chloroethyl, 2-cyanoethyl and 2-ethylhexyl. The alkyl group may be any of straight-chain, branched and cyclic types, which may have a substituent or may be unsubstituted. Preferable examples of the cycloalkyl group include substituted or unsubstituted cycloalkyl groups having 3 to 30 carbon atoms, for example, cyclohexyl, cyclopentyl, 4-n-dodecylcyclohexyl, bicyclo[1,2,2]heptane-2-yl and bicyclo[2,2,2]octane-3-yl and further include a tricyclo structure and the like having many cyclic structures. The alkyl groups (for example, an alkyl group in an alkylthio group) in the substituents described below represents alkyl groups having such a concept.

Preferable examples of the alkenyl group include alkenyl groups having 2 to 30 carbon atoms, for example, vinyl, allyl, pulenyl, geranyl and oleyl. The alkenyl group may be any of straight-chain, branched and cyclic types, which may have a substituent or unsubstituted. Preferable examples of the cycloalkenyl group include substituted or unsubstituted cycloalkenyl groups having 3 to 30 carbon atoms (monovalent groups obtained by removing one hydrogen atom from cycloalkenes having 3 to 30 carbon atoms), for example, 2-cyclopentene-1-yl, 2-cyclohexene-1-yl, bicyclo[2,2,1]hepto-2-ene-1-yl and bicyclo[2,2,2]octo-2-ene-4-yl), which may have a substituent or may be unsubstituted.

Preferable examples of the alkinyl group include alkinyl groups having 2 to 30 carbon atoms, for example, ethynyl, propalgyl and trimethylsylylethynyl groups, which may have a substituent or may be unsubstituted.

Preferable examples of the aryl group include aryl groups having 6 to 30 carbon atoms, for example, phenyl, p-tolyl, naphthyl, p-nitrophenyl, p-cyanophenyl, p-fluorophenyl, m-chlorophenyl and o-hexadecanoylaminophenyl, which may have a substituent or may be unsubstituted.

Preferable examples of the heterocyclic group include monovalent groups obtained by removing one hydrogen atom from five-membered or six-membered heterocyclic compounds and the heterocyclic group may be aromatic or non-aromatic. The heterocyclic group is more preferably heterocyclic groups having 3 to 30 carbon atoms. Examples of these heterocyclic groups include 2-furyl, 2-thienyl, 2-pyrimidinyl, 2-benzothiazolyl, quinolyl, thiazolyl, benzoxazolyl and benzoimidazolyl, which may have a substituent or may be unsubstituted.

Preferable examples of the alkoxy group include alkoxy groups having 1 to 30 carbon atoms, for example, methoxy, ethoxy, isopropoxy, t-butoxy, n-octyloxy and 2-methoxyethoxy, which may have a substituent or may be unsubstituted.

Preferable examples of the aryloxy group include aryloxy groups having 6 to 30 carbon atoms, for example, phenoxy, 2-methylphenoxy, 4-t-butylphenoxy, 3-nitrophenoxy and 2-tetradecanoylaminophenoxy, which may have a substituent or may be unsubstituted.

Preferable examples of the silyloxy group include silyloxy groups containing an organic group (an alkyl group and/or an aryl group) having 3 to 20 carbon atoms, for example, trimethylsilyloxy, t-butyldimethylsilyloxy and dimethylphenylsilyloxy.

Preferable examples of the heterocyclic oxy group include heterocyclic oxy groups having 2 to 30 carbon atoms, for example, 1-phenyltetrazole-5-oxy and 2-tetrahydropyranyloxy, which may have a substituent or may be unsubstituted.

Preferable examples of the acyloxy group include formyloxy groups, alkylcarbonyloxy groups having 2 to 30 carbon atoms and arylcarbonyloxy groups having 6 to 30 carbon atoms, for example, formyloxy, acetyloxy, pivaloyloxy, stearoyloxy, benzoyloxy and p-methoxyphenylcarbonyloxy, which may have a substituent or may be unsubstituted.

Preferable examples of the carbamoyloxy group include carbamoyloxy groups having 1 to 30 carbon atoms, for example, N,N-dimethylcarbamoyloxy, N,N-diethylcarbamoyloxy, morpholinocarbonyloxy, N,N-di-n-octylaminocarbonyloxy and N-n-octylcarbamoyloxy, which may have a substituent or may be unsubstituted.

Preferable examples of the alkoxycarbonyloxy group include alkoxycarbonyloxy groups having 2 to 30 carbon atoms, for example, methoxycarbonyloxy, ethoxycarbonyloxy, t-butoxycarbonyloxy and n-octylcarbonyloxy, which may have a substituent or may be unsubstituted.

Preferable examples of the aryloxycarbonyloxy group include aryloxycarbonyloxy groups having 7 to 30 carbon atoms, for example, phenoxycarbonyloxy, p-methoxyphenoxycarbonyloxy and p-n-hexadecyloxyphenoxycarbonyloxy, which may have a substituent or may be unsubstituted.

Preferable examples of the amino group include amino groups, alkylamino groups having 1 to 30 carbon atoms and anilino groups having 6 to 30 carbon atoms, for example, amino, methylamino, dimethylamino, anilino, N-methylanilino and diphenylamino, which may have a substituent or may be unsubstituted.

Preferable examples of the acylamino group include formylamino groups, alkylcarbonylamino groups having 1 to 30 carbon atoms and arylcarbonylamino groups having 6 to 30 carbon atoms, for example, formylamino, acetylamino, pivaloylamino, lauroylamino, benzoylamino and 3,4,5-tri-n-octyloxyphenylcarbonylamino, which may have a substituent or may be unsubstituted.

Preferable examples of the aminocarbonylamino group include aminocarbonylamino groups having 1 to 30 carbon atoms, for example, carbamoylamino, N,N-dimethylaminocarbonylamino, N,N-diethylaminocarbonylamino and morpholinocarbonylamino, which may have a substituent or may be unsubstituted.

Preferable examples of the alkoxycarbonylamino group include alkoxycarbonylamino groups having 2 to 30 carbon atoms, for example, methoxycarbonylamino, ethoxycarbonylamino, t-butoxycarbonylamino, n-octadecyloxycarbonylamino and N-methyl-methoxycarbonylamino, which may have a substituent or may be unsubstituted.

Preferable examples of the aryloxycarbonylamino group include aryloxycarbonylamino groups having 7 to 30 carbon atoms, for example, phenoxycarbonylamino, p-chlorophenoxycarbonylamino and m-(n-octyloxy)phenoxycarbonylamino, which may have a substituent or may be unsubstituted.

Preferable examples of the sulfamoylamino group include sulfamoylamino groups having 0 to 30 carbon atoms, for example, sulfamoylamino, N,N-dimethylaminosulfonylamino and N-n-octylaminosulfonylamino, which may have a substituent or may be unsubstituted.

Preferable examples of the alkyl or arylsulfonylamino group include alkylsulfonylamino groups having 1 to 30 carbon atoms and arylsulfonylamino groups having 6 to 30 carbon atoms, for example, methylsulfonylamino, butylsulfonylamino, phenylsulfonylamino, 2,3,5-trichlorophenylsulfonylamino and p-methylphenylsulfonylamino, which may have a substituent or may be unsubstituted.

Preferable examples of the alkylthio group include alkylthio groups having 1 to 30 carbon atoms, for example, methylthio, ethylthio and n-hexadecylthio, which may have a substituent or may be unsubstituted.

Preferable examples of the arylthio group include arylthio groups having 6 to 30 carbon atoms, for example, phenylthio, p-chlorophenylthio and m-methoxyphenylthio, which may have a substituent or may be unsubstituted.

Preferable examples of the heterocyclic thio group include heterocyclic thio groups having 2 to 30 carbon atoms, for example, 2-benzothiazolylthio and 1-phenyltetrazole-5-ylthio, which may have a substituent or may be unsubstituted.

Preferable examples of the sulfamoyl group include sulfamoyl groups having 0 to 30 carbon atoms, for example, N-ethylsulfamoyl, N-(3-dodecyloxypropyl) sulfamoyl, N,N-dimethylsulfamoyl, N-acetylsulfamoyl, N-benzoylsulfamoyl and N-(N'-phenylcarbamoyl)sulfamoyl, which may have a substituent or may be unsubstituted.

Preferable examples of the alkyl or arylsulfinyl group include alkylsulfinyl groups having 1 to 30 carbon atoms and arylsulfinyl groups having 6 to 30 carbon atoms, for example, methylsulfinyl, ethylsulfinyl, phenylsulfinyl and p-methylphenylsulfinyl, which may have a substituent or may be unsubstituted.

Preferable examples of the alkyl or arylsulfonyl group include alkylsulfonyl groups having 1 to 30 carbon atoms and arylsulfonyl groups having 6 to 30 carbon atoms, for example, methylsulfonyl, ethylsulfonyl, phenylsulfonyl and p-methylphenylsulfonyl, which may have a substituent or may be unsubstituted.

Preferable examples of the acyl group include formyl groups, alkylcarbonyl groups having 2 to 30 carbon atoms, arylcarbonyl groups having 7 to 30 carbon atoms and $C_4$-$C_{30}$ heterocyclic carbonyl groups with a hetero ring combined with a carbonyl group through a carbon atom, for example, acetyl, pivaloyl, 2-chloroacetyl, stearoyl, benzoyl, p-n-octyloxyphenylcarbonyl, 2-pyridylcarbonyl and 2-furylcarbonyl, which may have a substituent or may be unsubstituted.

Preferable examples of the aryloxycarbonyl group include aryloxycarbonyl groups having 7 to 30 carbon atoms, for example, phenoxycarbonyl, o-chlorophenoxycarbonyl, m-nitrophenoxycarbonyl and p-t-butylphenoxycarbonyl, which may have a substituent or may be unsubstituted.

Preferable examples of the alkoxycarbonyl group include alkoxycarbonyl groups having 2 to 30 carbon atoms, for example, methoxycarbonyl, ethoxycarbonyl, t-butoxycarbonyl and n-octadecyloxycarbonyl, which may have a substituent or may be unsubstituted.

Preferable examples of the carbamoyl group include carbamoyl groups having 1 to 30 carbon atoms, for example, carbamoyl, N-methylcarbamoyl, N,N-dimethylcarbamoyl, N,N-di-n-octylcarbamoyl and N-(methylsulfonyl)carbamoyl, which may have a substituent or may be unsubstituted.

Preferable examples of the aryl or heterocyclic azo group include arylazo groups having 6 to 30 carbon atoms and heterocyclic azo groups having 3 to 30 carbon atoms, for example, phenylazo, p-chlorophenylazo and 5-ethylthio-1,3,4-thiadiazole-2-ylazo, which may have a substituent or may be unsubstituted.

Preferable examples of the imide group include N-succinimide and N-phthalimide, which may have a substituent or may be unsubstituted.

Preferable examples of the phosphino group include phosphino groups having 2 to 30 carbon atoms, for example, dimethylphosphino, diphenylphosphino and methylphenoxyphosphino, which may have a substituent or may be unsubstituted.

Preferable examples of the phosphinyl group include phosphinyl groups having 2 to 30 carbon atoms, for example, phosphinyl, dioctyloxyphosphinyl and diethoxyphosphinyl, which may have a substituent or may be unsubstituted.

Preferable examples of the phosphinyloxy group include phosphinyloxy groups having 2 to 30 carbon atoms, for example, diphenoxyphosphinyloxy and dioctyloxyphosphinyloxy, which may have a substituent or may be unsubstituted.

Preferable examples of the phosphinylamino group include phosphinylamino groups having 2 to 30 carbon atoms, for example, dimethoxyphosphinylamino and dimethylaminophosphinylamino, which may have a substituent or may be unsubstituted.

Preferable examples of the silyl group include silyl groups having an organic group (an alkyl group and/or an aryl group) having 3 to 30 carbon atoms, for example, trimethylsilyl, t-butyldimethylsilyl and phenyldimethylsilyl, which may have a substituent or may be unsubstituted.

Among the aforementioned substituent group R, those having a hydrogen atom may be substituted further with the above group in place of the hydrogen atom. Examples of such a functional group include an alkylcarbonylaminosulfonyl group, arylcarbonylaminosulfonyl group, alkylsulfonylaminocarbonyl group and arylsulfonylaminocarbonyl group. Specific examples include a methylsulfonylaminocarbonyl, p-methylphenylsulfonylaminocarbonyl, acetylaminosulfonyl and benzoylaminosulfonyl group.

Also, $R_1$ and $R_2$, $R_4$ and $R_5$, $R_5$ and $R_6$ and $R_6$ and $R_7$ are respectively combined with each other to make a ring. When this ring is present, it is preferably a five-membered or six-membered ring constituted of a combination of $R_5$ and $R_6$, and may be a ring constituted only of carbon atoms or a hetero ring. In the case of a hetero ring, it is preferably a nitrogen-containing ring. Moreover, the ring may have a substituent. As the substituent, the same one as those explained for the above substituent group R may be used.

$R_1$ is preferably a halogen atom, a carbamoyl group, an acylamino group, an acyl group, an aryloxycarbonyl group or an alkoxycarbonyl group and particularly preferably a halogen atom or a carbamoyl group.

$R_2$, $R_3$, $R_4$, $R_5$ and $R_7$ are respectively preferably a hydrogen atom, a halogen atom, an alkyl group, an aryl group, an alkylthio group, an arylthio group, a heterocyclic thio group, a hydroxyl group, an alkoxy group, an aryloxy group, a carbamoyl group, an acyl group, an aryloxycarbonyl group, an alkoxycarbonyl group or an amide group and particularly preferably a hydrogen atom, a halogen atom, an alkyl group, an arylthio group or an amide group.

$R_6$ is preferably an amino group (including an alkylamino group and an arylarrino group), a hydroxyl group, a mercapto group, an alkylthio group, an arylthio group, an alkoxy group or an aryloxy group and particularly preferably an amino group.

Next, the substituent represented by the formula: —(Het)$_j$—((B1)$_p$—(Q1)$_q$—(B2)$_r$)$_n$—C1, will be explained in detail.

Het represents an oxygen atom or a sulfur atom and particularly preferably a sulfur atom.

B1 and B2 respectively represent a divalent aryl group, a heteroaryl group or a cyclic aliphatic hydrocarbon group.

The divalent aryl group is preferably an aryl group having 2 to 20 carbon atoms. Specific and preferable examples of the aryl group include a benzene ring, naphthalene ring and anthracene ring. A benzene ring and a substituted benzene ring are particularly preferable and 1,4-phenylene group is more preferable. The divalent heteroaryl group represented by B1 or B2 is preferably a heteroaryl group having 1 to 20 carbon atoms, for example, a pyridine ring, quinoline ring, isoquinoline ring, pyrimidine ring, pyrazine ring, thiophene ring, furan ring, oxazole ring, thiazole ring, imidazole ring, pyrazole ring, oxadiazole ring, thiadiazole ring, triazole ring and condensed cyclic heteroaryl groups produced by the condensation of these rings.

The divalent cyclic hydrocarbon group represented by B1 or B2 is preferably a cyclohexane-1,2-diyl group, a cyclohexane-1,3-diyl group, a cyclohexane-1,4-diyl group and cyclopentane-1,3-diyl group and particularly preferably a (E)-cyclohexane-1,4-diyl group.

The divalent cyclic hydrocarbon group represented by B1 or B2 may further have a substituent. Examples of the substituent include the following substituent group V.

Substituent Group V:

Examples of the substituent include a halogen atom (e.g., chlorine, bromine, iodine and fluorine), mercapto group, cyano group, carboxyl group, phosphoric acid group, sulfo group, hydroxy group, carbamoyl group having 1 to 10, preferably 2 to 8 and more preferably 2 to 5 carbon atoms, (for example, methylcarbamoyl, ethylcarbamoyl and morpholinocarbonyl), sulfamoyl group having 0 to 10, preferably 2 to 8 and more preferably 2 to 5 carbon atoms, (for example, methylsulfamoyl, ethylsulfamoyl and piperidinosulfonyl), nitro group, alkoxy group having 1 to 20, preferably 1 to 10 and more preferably 1 to 8 carbon atoms (for example, methoxy, ethoxy, 2-methoxyethoxy and 2-phenylethoxy), aryloxy group having 6 to 20, preferably 6 to 12 and more preferably 6 to 10 carbon atoms (for example, phenoxy, p-methylphenoxy, p-chlorophenoxy and naphthoxy), acyl group having 1 to 20, preferably 2 to 12 and more preferably 2 to 8 carbon atoms (for example, acetyl, benzoyl and trichloroacetyl), acyloxy group having 1 to 20, preferably 2 to 12 and more preferably 2 to 8 carbon atoms (for example, acetyloxy and benzoyloxy), acylamino group having 1 to 20, preferably 2 to 12 and more preferably 2 to 8 carbon atoms (for example, acetylamino), sulfonyl group having 1 to 20, preferably 1 to 10 and more preferably 1 to 8 carbon atoms (for example, methanesulfonyl, ethanesulfonyl and benzenesulfonyl), sulfinyl group having 1 to 20, preferably 1 to 10 and more preferably 1 to 8 carbon atoms (for example, methanesulfinyl, ethanesulfinyl and benzenesulfinyl), substituted or unsubstituted amino group having 1 to 20, preferably 1 to 12 and more preferably 1 to 8 carbon atoms (for example, amino, methylamino, dimethylamino, benzylamino, anilino, diphenylamino, 4-methylphenylamino, 4-ethylphenylamino, 3-n-propylphenylamino, 4-n-propylphenylamino, 3-n-butylphenylamino, 4-n-butylphenylamino, 3-n-pentylphenylamino, 4-n-pentylphenylamino, 3-trifluoromethylphenylamino, 4-trifluoromethylphenylamino, 2-pyridylamino, 3-pyridylamino, 2-thiazolylamino, 2-oxazolylamino, N,N-methylphenylamino and N,N-ethylphenylamino), ammonium group having 0 to 15, preferably 3 to 10 and more preferably 3 to 6 carbon atoms (for example, trimethylammonium and triethylammonium), hydrazino group having 0 to 15, preferably 1 to 10 and more preferably 1 to 6 carbon atoms (for example, trimethylhydrazino group), ureide group having 1 to 15, preferably 1 to 10 and more preferably 1 to 6 carbon atoms (for example, an ureide group and N,N-dimethylureide group), imide group having 1 to 15, preferably 1 to 10 and more preferably 1 to 6 carbon atoms (for example, a succinimide group), alkylthio group having 1 to 20, preferably 1 to 12 and more preferably 1 to 8 carbon atoms (for example, methylthio, ethylthio and propylthio), arylthio group having 6 to 80, preferably 6 to 40 and more preferably 6 to 30 carbon atoms (for example, phenylthio, p-methylphenylthio, p-chlorophenylthio, 2-pyridylthio, 1-naphthylthio, 2-naphthylthio, 4-propylcyclohexyl-4'-biphenylthio, 4-butylcyclohexyl-4'-biphenylthio, 4-pentylcyclohexyl-4'-biphenylthio and 4-propylphenyl-2-ethynyl-4'-biphenylthio), heteroarylthio group having 1 to 80, preferably 1 to 40 and more preferably 1 to 30 carbon atoms (for example, 2-pyridylthio, 3-pyridylthio, 4-pyridylthio, 2-quinolylthio, 2-furylthio and 2-pyrrolylthio), alkoxycarbonyl group having 2 to 20, preferably 2 to 12 and more preferably 2 to 8 carbon atoms (for example, methoxycarbonyl, ethoxycarbonyl and 2-benzyloxycarbonyl), aryloxycarbonyl group having 6 to 20, preferably 6 to 12 and more preferably 6 to 10 carbon atoms (for example, phenoxycarbonyl), unsubstituted alkyl group having 1 to 18, preferably 1 to 10 and more preferably 1 to 5 carbon atoms (for example, methyl, ethyl, propyl and butyl), substituted alkyl group having 1 to 18, preferably 1 to 10 and more preferably 1 to 5 carbon atoms (for example, hydroxymethyl, trifluoromethyl, benzyl, carboxyethyl, ethoxycarbonylmethyl and acetylaminomethyl, also, here, unsaturated hydrocarbon groups having 2 to 18, preferably 3 to 10 and more preferably 3 to 5 carbon atoms (for example, a vinyl group, ethynyl group, 1-cyclohexenyl group, benzylidyne group and benzylidene group) are also included), substituted or unsubstituted aryl groups having 6 to 20, preferably 6 to 15 and more preferably 6 to 10 carbon atoms (for example, phenyl, naphthyl, p-carboxyphenyl, p-nitrophenyl, 3,5-dichlorophenyl, p-cyanophenyl, m-fluorophenyl, p-tolyl, 4-propylcyclohexyl-4'-biphenyl, 4-butylcyclohexyl-4'-biphenyl, 4-pentylcyclohexyl-4'-biphenyl and 4-propylphenyl-2-ethynyl-4'-biphenyl) and substituted or unsubstituted heteroaryl group having 1 to 20, preferably 2 to 10 and more preferably 4 to 6 carbon atoms (for example, pyridyl, 5-methylpyridyl, thienyl, furyl, morpholino and tetrahydrofurfuryl).

The substituent group V may take a structure in which a benzene ring or a naphthalene ring is condensed. Further, these substituents may be substituted with the substituents explained before in V.

As the substituent group V, the aforementioned alkyl group, aryl group, alkoxy group, aryloxy group, halogen atom, amino group, substituted amino group, hydroxy group, alkylthio group and arylthio group are preferable and an alkyl group, aryl group and halogen atom are more preferable.

Q1 represents a divalent connecting group. Q1 preferably comprises an atomic group constituted of a carbon atom, nitrogen atom, sulfur atom and oxygen atom. Examples of the divalent connecting group include divalent connecting groups having 0 to 60 carbon atoms and constituted of one or a combination of two or more of an alkylene group having 1 to 20 carbon atoms (for example, methylene, ethylene, propylene, butylene, pentylene, cyclohexyl-1,4-diyl), alkenylene group having 2 to 20 carbon atoms (for example, ethenylene), alkinylene group having 2 to 20 carbon atoms (for example, ethynylene), amide group, ether group, ester group, sulfoamide group, sulfonate group, ureide group, sulfonyl group, sulfinyl group, thioether group, carbonyl group, —NR-group (where R represents a hydrogen atom, an alkyl group or an aryl group), azo group, azoxy group and heterocyclic divalent group (for example, a piperazine-1,4-diyl group). The divalent connecting group represented by Q1 is preferably an alkylene group, alkenylene group, alkinylene group, ether group, thioether group, amide group, ester group, carbonyl group or a combination of these groups. Q1 may further have a substituent. Examples of the substituent include the above substituent group V.

C1 represents an alkyl group, a cycloalkyl group, an alkoxy group, an alkoxycarbonyl group, an acyl group or an acyloxy group. Preferable examples of C1 include an alkyl or cycloalkyl group having 1 to 30, preferably 1 to 12 and more preferably 1 to 8 carbon atoms (for example, methyl, ethyl, propyl, butyl, t-butyl, i-butyl, s-butyl, pentyl, t-pentyl, hexyl, heptyl, octyl, cyclohexyl, 4-methylcyclohexyl, 4-ethylcyclohexyl, 4-propylcyclohexyl, 4-butylcyclohexyl, 4-pentylcyclohexyl, hydroxymethyl, trifluoromethyl and benzyl), alkoxy group having 1 to 20, preferably 1 to 10 and more preferably 1 to 8 carbon atoms (for example, methoxy, ethoxy, 2-methoxyethoxy and 2-phenylethoxy), acyloxy group having 1 to 20, preferably 2 to 12 and more preferably 2 to 8 carbon atoms (for example, acetyloxy and benzoyloxy), acyl group having 1 to 30, preferably 1 to 12 and more preferably 1 to 8 carbon atoms (for example, acetyl, formyl group, pivaloyl, 2-chloroacetyl, stearoyl, benzoyl, p-n-octyloxyphenylcarbonyl) and alkoxycarbonyl group having 2 to 20, preferably 2 to 12 and more preferably 2 to 8 carbon atoms (for example, methoxycarbonyl, ethoxycarbonyl and 2-benzylox-ycarbonyl). C1 is particularly preferably an alkyl group or an alkoxy group and more preferably an ethyl group, a propyl group, a butyl group, a pentyl group, a hexyl group or a trifluoromethoxy group. C1 may further have a substituent and examples of the substituent include the aforementioned substituent group V.

j denotes a number 0 or 1 and preferably 0.

p, q and r respectively denote an integer from 0 to 5 and n denotes an integer from 1 to 3, provided that (p+r)×n is a number of 3 or more and 10 or less. In the case where p, q and r are respectively 2 or more, B1s, Q1s and B2s may be respectively the same or different. Also, when n is 2 or more, $n((B1)_p—(Q1)_q—(B2)_r)$s may be the same or different.

Preferable combinations of p, q, r and n are shown below.
(i) p=3, q=0, r=0 and n=1.
(ii) p=4, q=0, r=0 and n=1.
(iii) p=5, q=0, r=0 and n=1.
(iv) p=2, q=0, r=1 and n=1.
(v) p=2, q=1, r=1 and n=1.
(vi) p=1, q=1, r=2 and n=1.
(vii) p=3, q=1, r=1 and n=1.
(viii) p=2, q=0, r=2 and n=1.
(ix) p=1, q=1, r=1 and n=2.
(x) p=2, q=1, r=1 and n=2.

Particularly preferable combinations are as follows: (i) p=3, q=0, r=0 and n=1, (iv) p=2, q=0, r=1 and n=1 and (v) p=2, q=1, r=1 and n=1.

$((B1)_p—(Q1)_q—(B2)_r)_n$—C1 preferably has a structure having liquid crystallinity. The liquid crystal here is preferably a nematic liquid crystal, smectic liquid crystal or discotheque liquid crystal and particularly preferably nematic liquid crystal though it may be any phase.

Specific examples of liquid crystal compounds include those described in Liquid Crystal Handbook edited by Liquid Crystal Handbook Editing Committee, Maruzen, (2000), Chapter No. 3, "Molecular structure and Liquid crystallinity".

Specific examples of $((B1)_p—(Q1)_q—(B2)_r)_n$—C1 will be shown below: however, these examples are not intended to be limiting of the present invention (the broken line shows the connecting position in the figure)

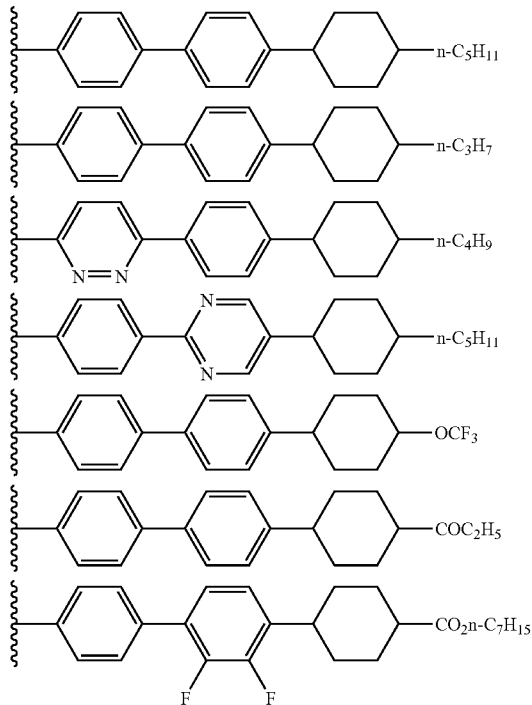

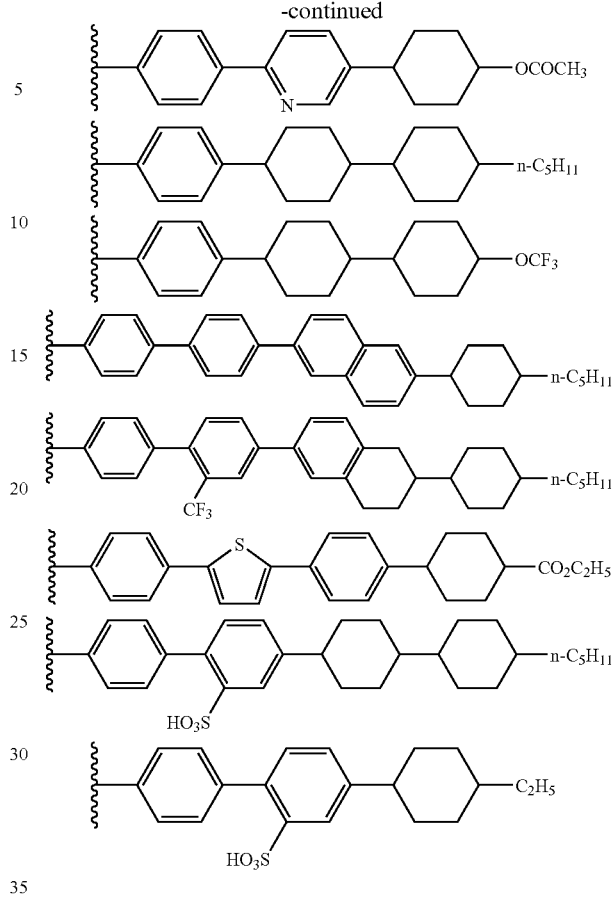

The number of substituents represented by $((B1)_p—(Q1)_q—(B2)_r)_n$—C1 may be any of 1 to 8, but is preferably 1 to 4 and particularly preferably 1 or 2.

Preferable examples of the structure of the substituent represented by the formula (3) may include the following two structures.

(1) Structure in which Het represents a sulfur atom, B1 represents an aryl group or a heteroaryl group, B2 represents a cyclohexane-1,4-diyl group, C1 represents an alkyl group, j=1, p=2, q=0, r=1 and n=1.

(2) Structure in which Het represents a sulfur atom, B1 represents an aryl group or a heteroaryl group, B2 represents a cyclohexane-1,4-diyl group, C1 represents an alkyl group, j=1, p=1, q=0, r=2 and n=1.

Particularly preferable examples of the structure of the substituent represented by the formula (3) include the following structures.

(I) Structure in which Het represents a sulfur atom, B1 represents a 1,4-phenylene group, B2 represents a trans-cyclohexane-1,4-diyl group, C1 represents an alkyl group (preferably a methyl group, ethyl group, propyl group, butyl group, pentyl group or hexyl group), j=1, p=2, q=0, r=1 and n=1 and which is represented by the following formula (a-1).

(II) Structure in which Het represents a sulfur atom, B1 represents a 1,4-phenylene group, B2 represents a trans-cyclohexane-1,4-diyl group, C1 represents an alkyl group (preferably a methyl group, ethyl group, propyl group, butyl group, pentyl group or hexyl group), j=1, p=1, q=0, r=2 and n=1 and which is represented by the following formula (a-2).

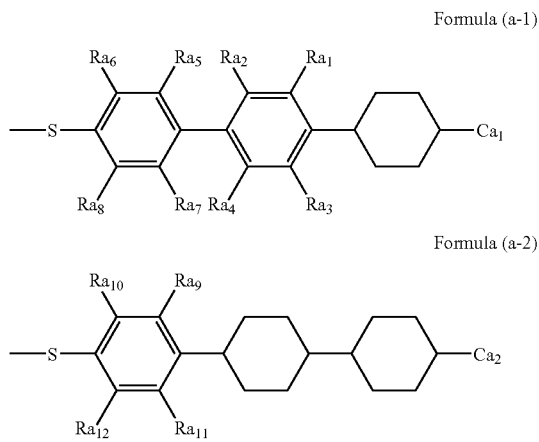

Formula (a-1)

Formula (a-2)

In the above formulae (a-1) and (a-2), $Ra_1$ to $Ra_{12}$ each independently represent a hydrogen atom or a substituent. Examples of the substituent include substituents selected from the aforementioned substituent group V. $Ra_1$ to $Ra_{12}$ respectively preferably represent a hydrogen atom, a halogen atom (particularly, a fluorine atom), an alkyl group, an aryl group or an alkoxy group.

In the above formulae (a-1) and (a-2), $Ca_1$ and $Ca_2$ each independently represent an alkyl group and preferably a methyl group, an ethyl group, a propyl group, a butyl group, a pentyl group or a hexyl group.

Specific examples of the formula (1) will be shown below: however, these examples are not intended to be limiting of the present invention.

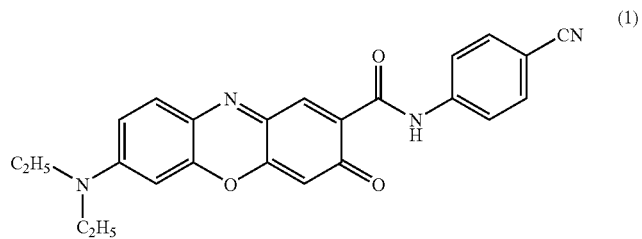

(1)

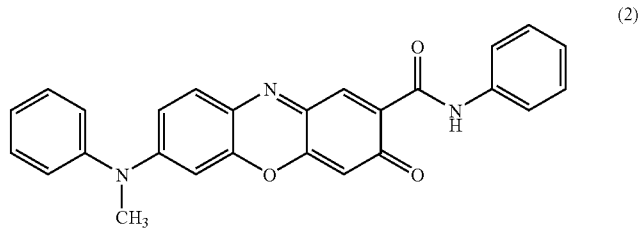

(2)

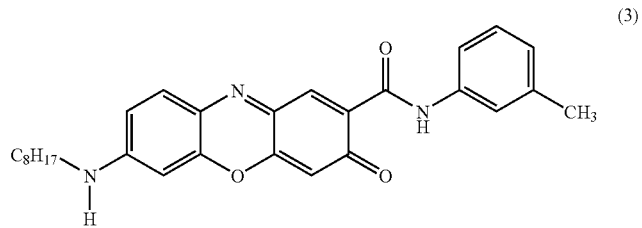

(3)

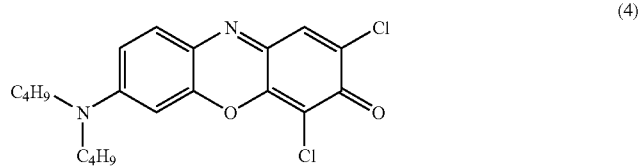

(4)

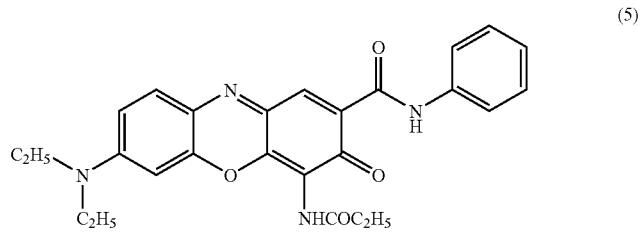

(5)

-continued
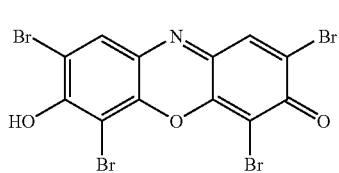
(6)
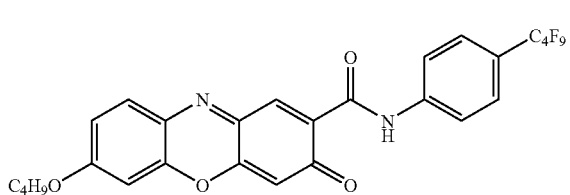
(7)
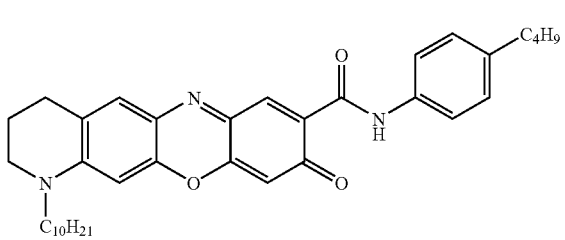
(8)
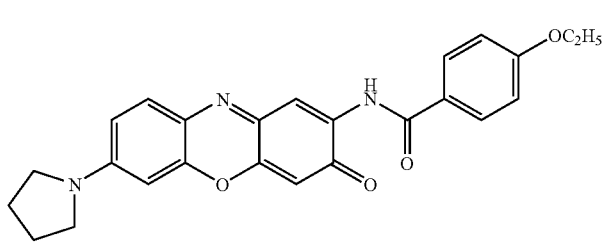
(9)
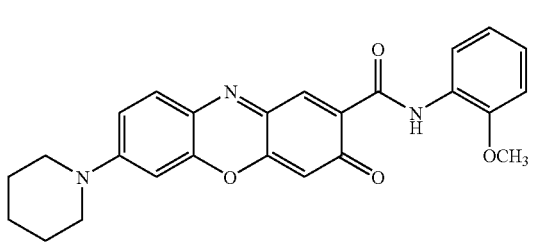
(10)
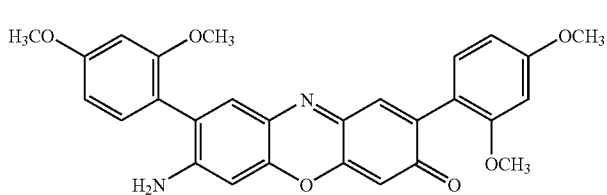
(11)
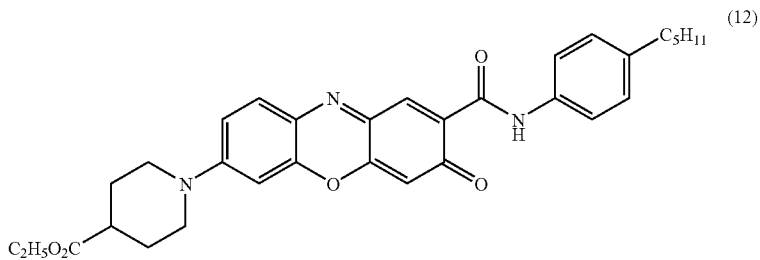
(12)

-continued
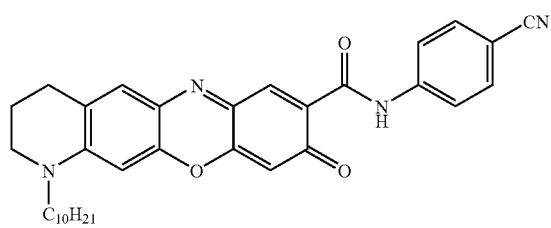
(13)
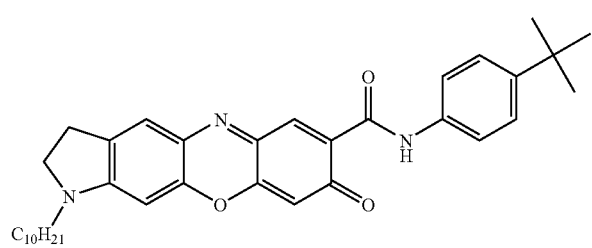
(14)
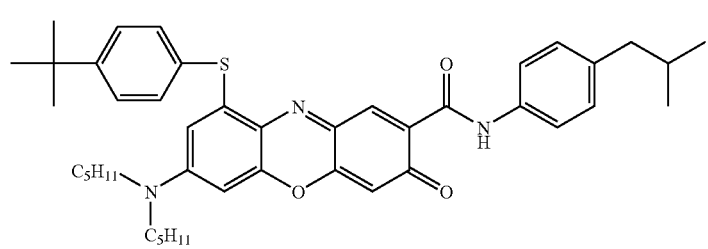
(15)
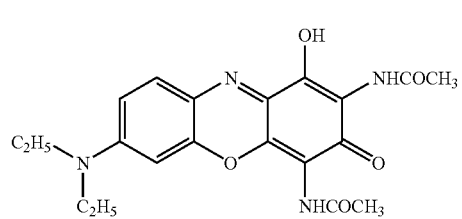
(16)
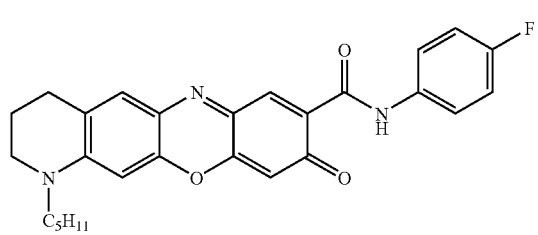
(17)
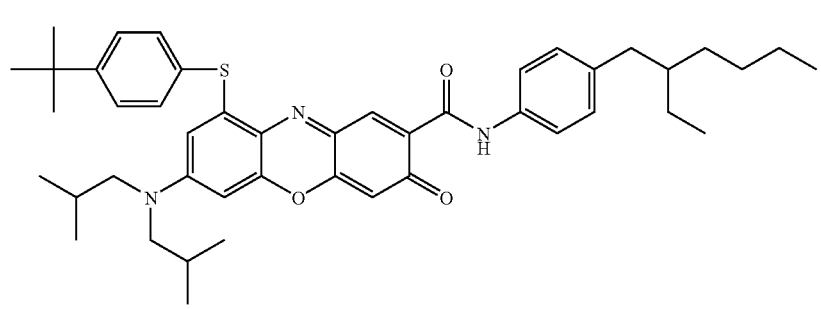
(18)

-continued
(19)
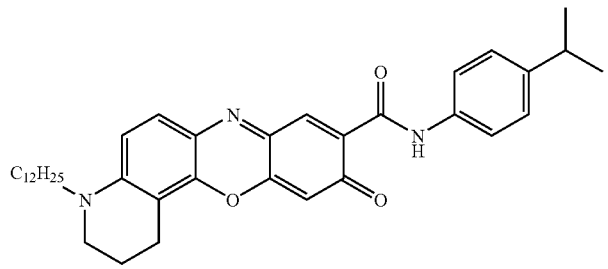
(20)
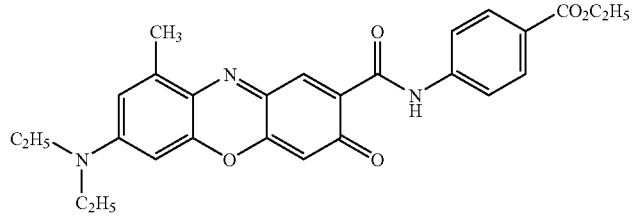
(21)
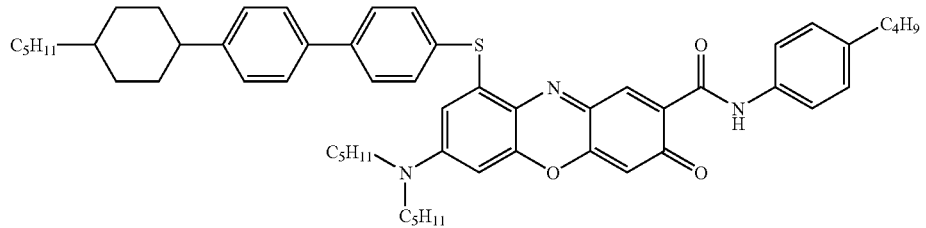
(22)
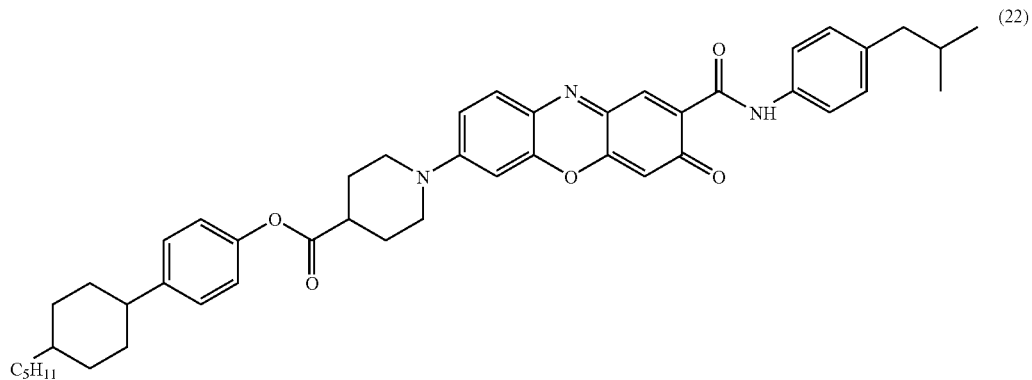
(23)
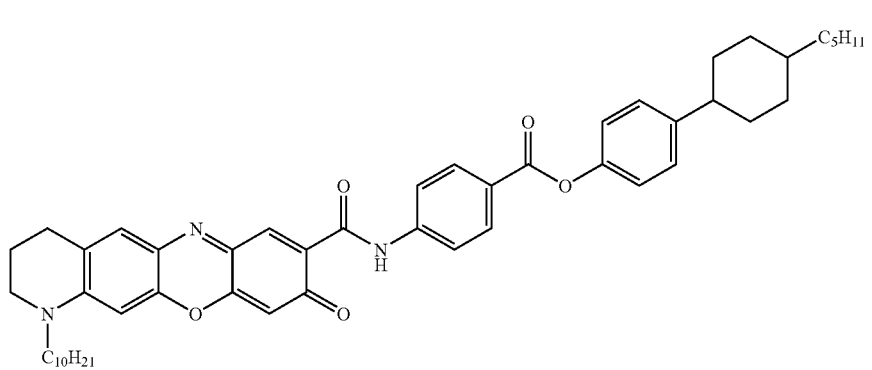

-continued
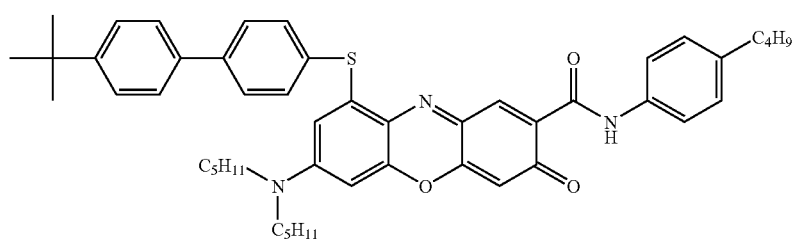
(24)
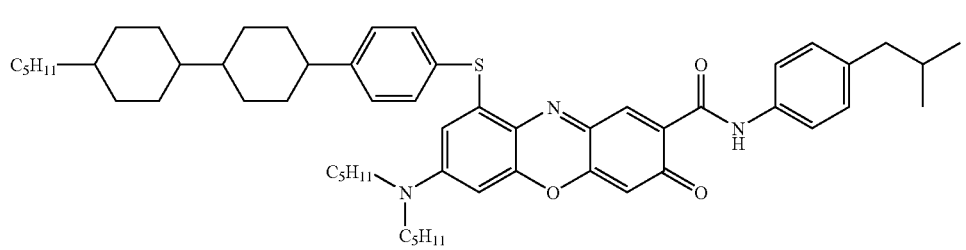
(25)
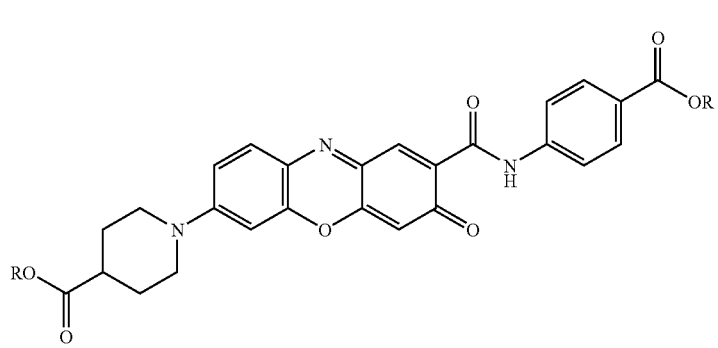
(26)
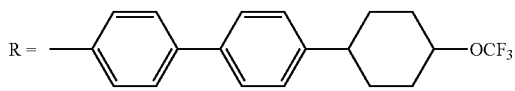
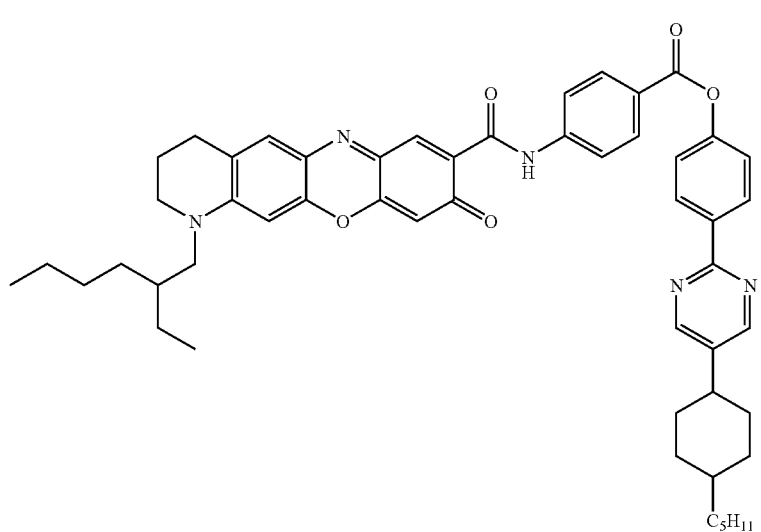
(27)

-continued

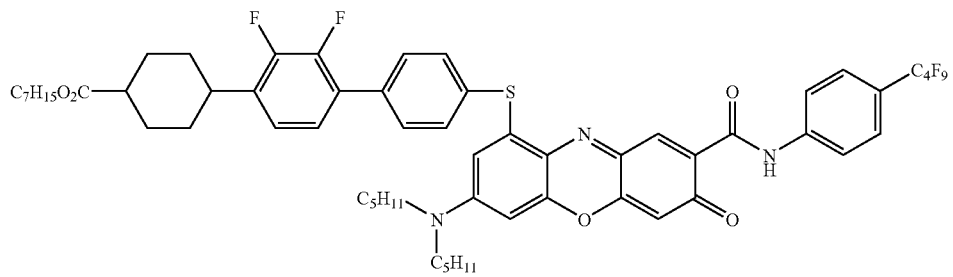
(28)

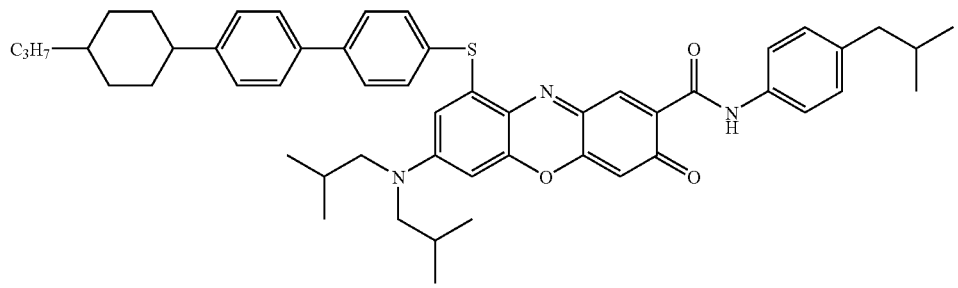
(29)

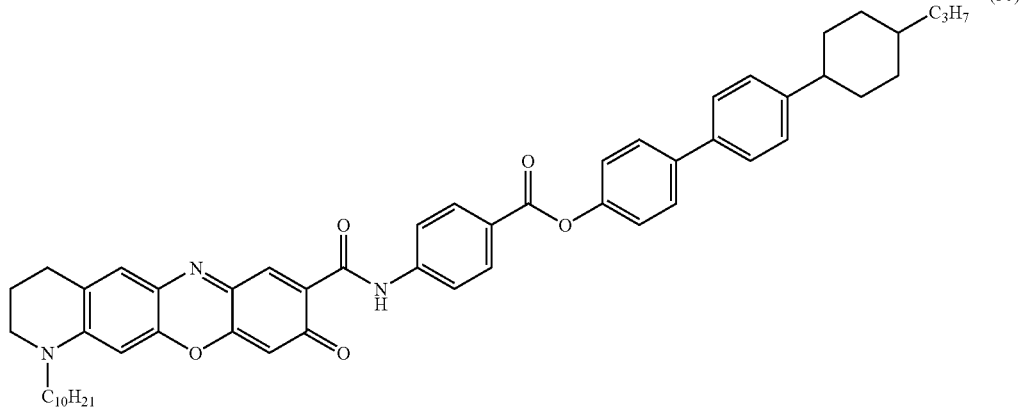
(30)

A specific method of synthesizing the compound represented by the formula (1) will be mentioned hereinbelow.

<Synthesis of Compound Example (1)>
A compound example (1) is synthesized according to the following scheme.

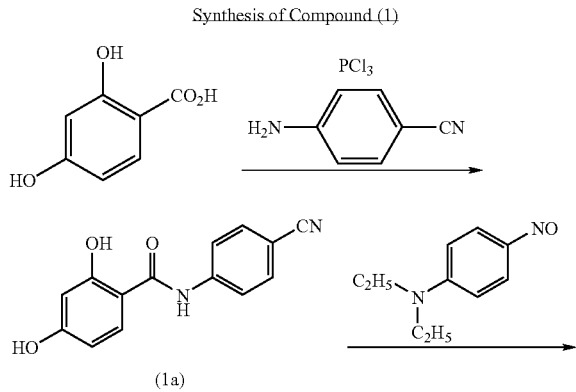

-continued

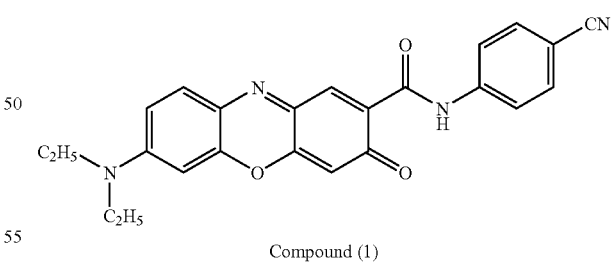
Compound (1)

(Synthesis of Compound (1a))

Phosphorous trichloride (4.4 g) was added dropwise to an N-methylpyrrolidone solution (50 ml) containing 2,4-dihydroxybenzoic acid (5 g) and 4-cyanoaniline (11 g) at 60° C. and the mixture is stirred for 10 hours. The reaction solution is poured into a sodium hydrogencarbonate aqueous solution. The precipitated crystals are collected by filtration and recrystallized from ethyl acetate/hexane to obtain a compound 1a (5.8 g).

(Synthesis of the Exemplified Compound (1))

An acetic acid solution (10 ml) containing the compound 1a (1.4 g) and 4-diethylamino-1-nitrosobenzene (1 g) is stirred for one hour under heating and refluxing. The reaction solution is poured into water and the precipitated crystals were collected by filtration. The collected crystals are purified by silica gel column chromatography (developing solvent: chloroform/methanol=9/1) to obtain the exemplified compound 1 (1.7 g). The compound is identified by the elemental analysis and the measurement of NMR and MASS spectrum.

λmax=629 nm, ε=95000 (DMF solution)

<Synthesis of Compound Example (8)>

A compound example (8) is synthesized according to the following scheme.

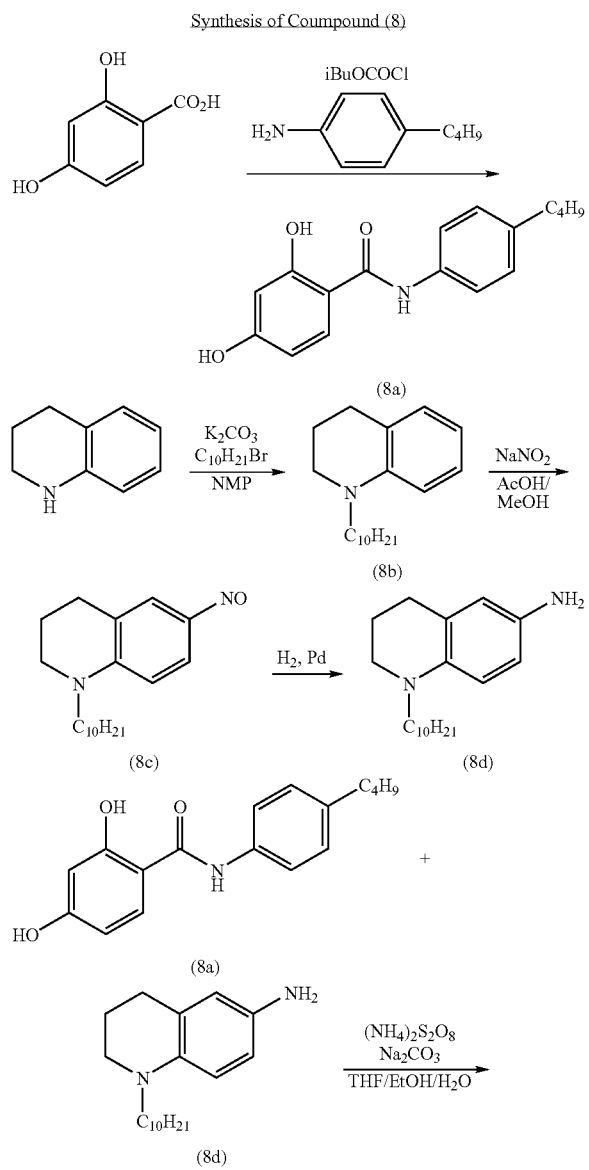

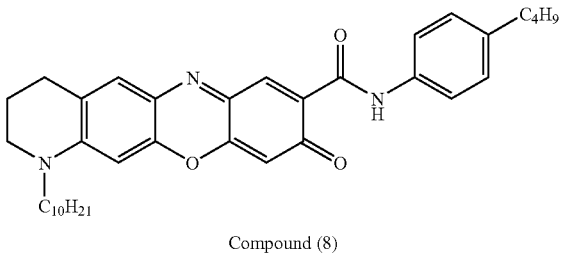

Compound (8)

(Synthesis of Compound (8a))

Triethylamine (20.4 g) is added dropwise to an ethyl acetate solution (100 ml) containing 2,4-dihydroxybenzoic acid (10 g) and isobutyl chlorocarbonate (27.5 g) at 0° C. After the mixture is stirred for 3 hours, an ethyl acetate solution (20 ml) containing 4-butylaniline (10.7 g) is added dropwise to the mixture, which is then stirred for 5 hours. The reaction solution is poured into 1N hydrochloric acid aqueous solution (200 ml). The organic phase is washed with hydrochloric acid aqueous solution, dried using magnesium sulfate and then concentrated under reduced pressure. The concentrated residue is dissolved in methanol (20 ml), to which is then added a sodium hydroxide (5.2 g) aqueous solution (50 ml), followed by stirring at 60° C. for 3 hours. The reaction solution is poured into an ethyl acetate/sodium carbonate aqueous solution. The organic phase is washed with water, dried by magnesium sulfate and then concentrated under reduced pressure. The precipitated crystals are collected by filtration and recrystallized from ethyl acetate/hexane to obtain a compound 8a (13 g).

(Synthesis of Compound (8b))

An N-methylpyrrolidone solution (500 ml) containing 1,2,3,4-tetrahydroquinoline (50 g), decyl bromide (115 g) and sodium bicarbonate (67 g) is stirred at 150° C. for 3 hours. The reaction solution is poured into an ethyl acetate/ 1N hydrochloric acid aqueous solution. The organic phase is washed with 1N hydrochloric acid aqueous solution, dried by magnesium sulfate and then concentrated under reduced pressure. The concentrated residue is purified by silica gel column chromatography (developing solvent: ethyl acetate/ hexane=1/30) to obtain a compound 8b (93 g).

(Synthesis of Compound (8c))

A sodium nitrite (13.8 g) aqueous solution (30 ml) is added dropwise to a solution mixture of concentrated hydrochloric acid (43 ml) and methanol (250 ml) containing the compound 8b (45 g) at 10° C. After the mixture is stirred for one hour, the reaction solution is poured into a methylene chloride/sodium bicarbonate aqueous solution and the organic phase is washed with saturated brine. The organic phase is then purified by silica gel column chromatography (developing solvent: ethyl acetate/hexane=1/4) to obtain a compound 8c (41.3 g).

(Synthesis of Compound (8d))

10 wt % Pd/C (0.5 g) is added as a catalyst to a solution mixture of methanol (90 ml) and tetrahydrofuran (18 ml) containing the compound 8c (15 g). The mixture is stirred at room temperature for 24 hours in a atmospheric pressure hydrogen atmosphere. After the catalyst is removed, a methanol solution of 1,5-naphthalenedisulfonic acid tetrahydrate (18 g) is added to the solution, which was then concentrated under reduced pressure. The precipitated crystals are washed with methanol to thereby obtain 1,5-naphthalene disulfonate of a compound 8d (24 g).

(Synthesis of the Exemplified Compound (8))

An aqueous solution (40 ml) containing ammonium persulfate (3.2 g) and sodium carbonate (3.7 g) is added dropwise to a solution mixture of ethanol (200 ml) and THF (200 ml) containing the compound 8a (1 g) and the 1,5-naphthalenedisulfonate of the compound 8d (2.6 g) and the mixture is stirred for one hour. The reaction solution is poured into chloroform/1N hydrochloric acid aqueous solution. The organic phase is dried by magnesium sulfate and then concentrated under reduced pressure. The concentrated residue is purified by silica gel column chromatography (developing solvent: chloroform/methanol=20/1) to thereby obtain the exemplified compound 8 (1.3 g). The compound is identified by the elemental analysis and the measurement of NMR and MASS spectrum.

$^1$H-NMR (CDCl$_3$)

δ: 0.88 (3H, t), 0.93 (3H, t), 1.22-1.77 (20H, m), 2.00 (2H, m), 2.58 (2H, t), 2.86 (2H, dt), 3.42 (2H, dt), 3.50 (2H, dt), 6.42 (2H, d), 7.14 (2H, d), 7.39 (1H, s), 7.69 (2H, d), 8.58 (1H, s), 12.19 (1H, s)

λmax=637.5 nm, ε=119000 (DMF solution)
λmax=625.5 nm, ε=118000 (CHCl$_3$ solution)

Among compounds according to the present invention, a compound represented by the following formula (4) is a novel compound. This compound was found as one of preferable compounds for the purpose of the present invention.

Formula (4)

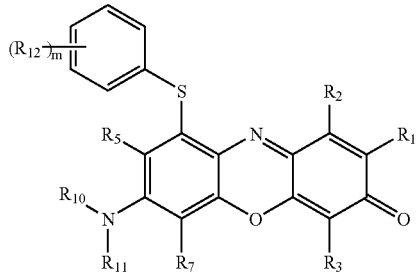

wherein $R_1$, $R_2$, $R_3$, $R_5$ and $R_7$ each independently represent a hydrogen atom or a substituent; $R_{10}$ and $R_{11}$ each independently represent a hydrogen atom, an alkyl group or an aryl group; $R_{12}$ represents a substituent; and m represents an integer from 0 to 5.

$R_1$, $R_2$, $R_3$, $R_5$ and $R_7$ have the same meanings as those explained in the formulae (1) and (2). Also, $R_{12}$ is preferably a halogen atom, an alkyl group, an aryl group, a heterocyclic group, an alkoxy group, an aryloxy group, an acyl group, an aryloxycarbonyl group or an alkoxycarbonyl group and more preferably an alkyl group, an aryl group or a heterocyclic group. m denotes an integer from 0 to 5 and is preferably 0 or 1.

$R_{10}$ and $R_{11}$ each independently represent a hydrogen atom, an alkyl group or an aryl group and are respectively preferably an alkyl group. Also, when $R_{10}$ and $R_{11}$ are respectively an alkyl group or an aryl group, $R_{10}$ and $R_{11}$, $R_{10}$ and $R_5$, or $R_{11}$ and $R_7$ may be respectively combined with each other to make a ring. When this ring is present, it is preferably a five-membered or six-membered ring. Moreover, the ring may have a substituent. As the substituent, the same one as those explained for the above substituent group R may be used.

In the present invention, compounds (21) and (24) which are the compounds represented by the formula (4) are synthesized according to the following synthetic method.

<Synthesis of Compound Example (21)>

A compound example (21) is synthesized according to the following scheme.

Synthesis of Compound (21)

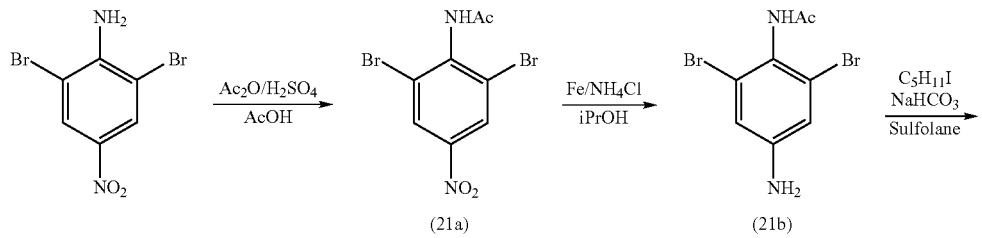

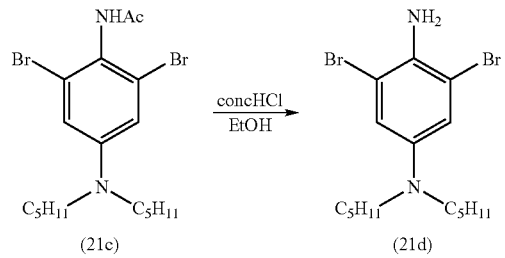

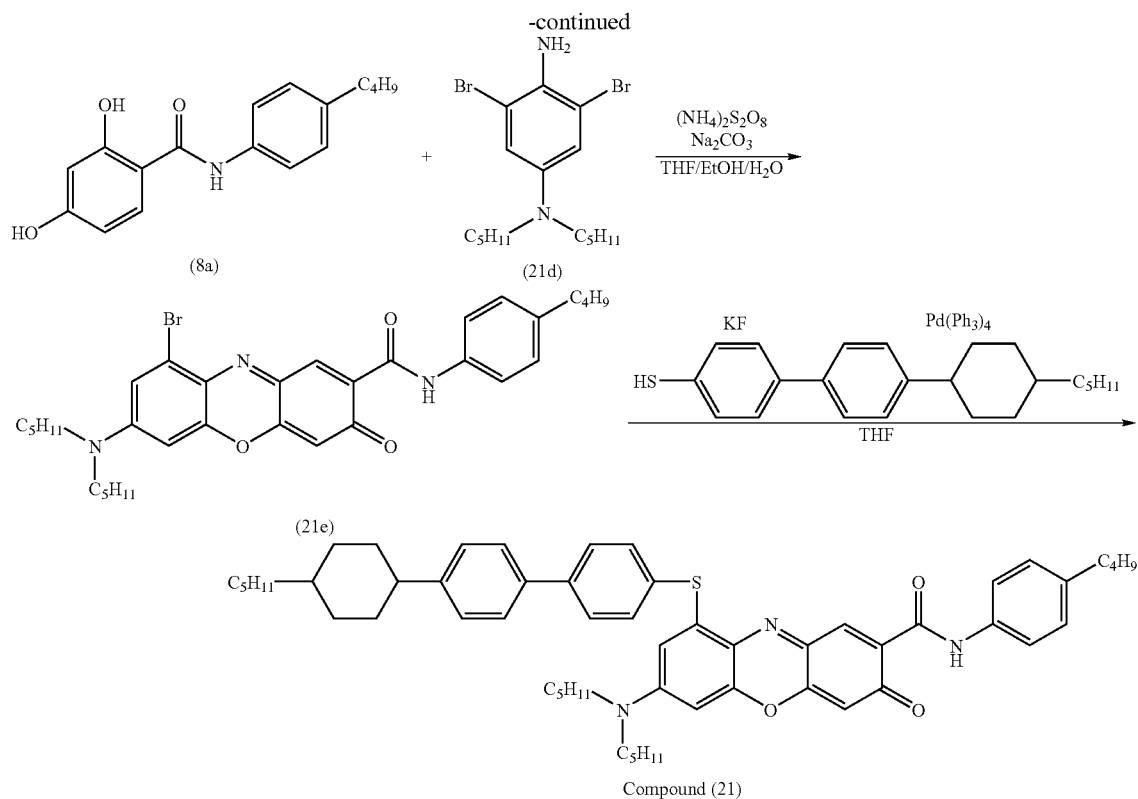

Compound (21)

(Synthesis of Compound (21a))

Acetic acid anhydride (173 g) is added to an acetic acid solution (500 ml) containing 2,6-dibromo-4-nitroaniline (50 g). Then, concentrated sulfuric acid (4 ml) is added dropwise to the mixture, which is then stirred for one hour. The reaction solution is poured into 1 L of water and the precipitated crystals are collected to obtain a compound 21a (52 g).

(Synthesis of Compound (21b))

The compound 21a (50 g) is added to a solution mixture of isopropyl alcohol (500 ml) and water (50 ml) containing reducing iron (58 g) and ammonium chloride (7.9 g) under heating and refluxing and the mixture is stirred for one hour. The reaction solution is subjected to filtering using celite and the resulting filtrate is concentrated under reduced pressure. Water is added to the concentrated residue and the precipitated crystals are collected by filtration to thereby obtain a compound 21b (37 g).

(Synthesis of Compound (21c))

A sulfolane solution (200 ml) containing the compound 21b (20 g), n-iodopentane (26 g) and sodium bicarbonate (18 g) is stirred at 150° C. for 10 hours in a nitrogen stream. The reaction solution is poured into water, and the precipitated crystals are collected by filtration and then recrystallized from ethyl acetate to obtain a compound 21 c (18 g).

(Synthesis of Compound (2 d))

Concentrated hydrochloric acid (10 ml) is added to an ethanol solution (50 ml) containing the compound 21c (5 g) and the mixture is stirred under heating and refluxing for 10 hours. The reaction solution is poured into an ethyl acetate/ sodium bicarbonate aqueous solution. The organic phase is washed with water, dried using magnesium sulfate and then concentrated under reduced pressure. A methanol solution of 1,5-naphthalenedisulfonic acid tetrahydrate (3.8 g) is added to the concentrated residue, which is then concentrated under reduced pressure. The precipitated crystals are washed with methanol to obtain a 1,5-naphthalenedisulfonate of a compound 21d (5.4 g).

(Synthesis of Compound (21e))

An aqueous solution (200 ml) containing ammonium persulfate (1.8 g) and sodium carbonate (2.1 g) is added dropwise to a solution mixture of ethanol (200 ml) and THF (200 ml) containing the compound 8a (0.57 g) and the 1,5-naphthalenedisulfonate of the compound 21d (2 g) and the mixture is stirred for 2 hours. The reaction solution is poured into chloroform/water, which is neutralized by adding 1N hydrochloric acid aqueous solution. The organic phase is dried using magnesium sulfate and then concentrated under reduced pressure. The precipitated crystals are washed with n-hexane (50 ml)/ethyl acetate (10 ml) to obtain a compound 21e (1 g). The compound is identified by the elemental analysis and the measurement of NMR and MASS spectrum.

(Synthesis of the Exemplified Compound (21))

Tetrakistriphenylphosphinpalladium (0.19 g) is added to a THF solution (15 ml) containing the compound 21e (1 g), the following compound 2 (0.56 g) (the compound 2 is obtained by the synthesis method described in JP-A No. 2003-192664, Paragraph Nos. 0064 to 0066) and potassium fluoride (0.24 g) and the mixture is stirred at room temperature in a nitrogen atmosphere for 24 hours. The reaction solution is poured into chloroform/water and neutralized by 1N hydrochloric acid aqueous solution. The organic phase is dried using magnesium sulfate and then concentrated under reduced pressure. The concentrated organic phase was purified by silica gel column chromatography (developing solvent: ethyl acetate/chloroform=1/10) to obtain the exemplified compound 21 (0.86 g). The compound was identified by the elemental analysis and the measurement of NMR and MASS spectrum.

Compound 2

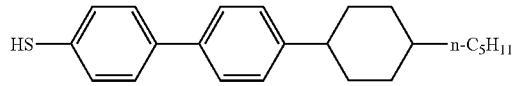

$^1$H-NMR (CDCl$_3$)

δ: 0.78 (6H, m), 0.90 (3H, t), 0.93 (3H, t), 0.98-1.63 (29H, m), 1.91 (4H, t), 2.53 (1H, t), 2.59 (2H, t), 3.14 (4H, m), 5.88 (1H, s), 6.18 (1H, s), 6.42 (1H, s), 7.16 (2H, d), 7.32 (2H, d), 7.56 (2H, d), 7.67-7.76 (6H, m), 8.69 (1H, s), 12.08 (1H, s)

λmax=635.2 nm, ε=105000 (DMF solution)
λmax=624.5 nm, ε=103000 (CHCl$_3$ solution)

<Synthesis of Compound Example (24)>

A compound example (24) was synthesized according to the following scheme.

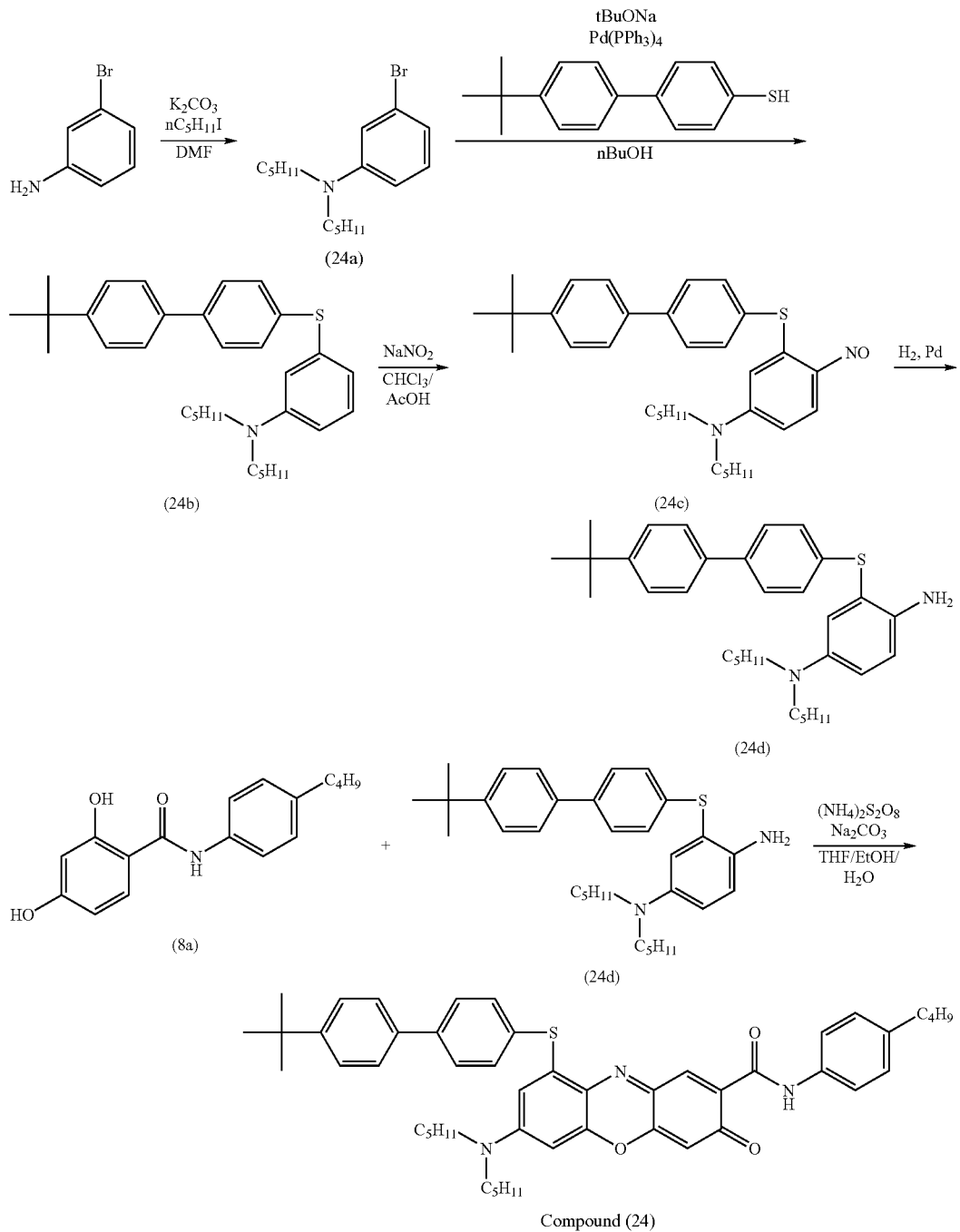

Compound (24)

(Synthesis of Compound (24a))

A DMF solution (80 ml) containing m-bromoaniline (20 g), iodopentane (55 g) and potassium carbonate (45 g) is stirred at 100° C. for 5 hours. The reaction solution is poured into ethyl acetate/water. The organic phase is dried using magnesium sulfate and then concentrated under reduced pressure. The concentrated residue is purified by silica gel column chromatography (developing solvent: hexane) to obtain a compound 24a (26 g).

(Synthesis of Compound (24b))

Tetrakistriphenylphosphinpalladium (1.5 g) is added to an n-butyl alcohol solution containing the compound 24a (5.2 g), 4'-t-butylbiphenyl-4-thiol (4 g) and t-butoxysodium (3.2 g) and the mixture is stirred under heating and refluxing for 10 hours. Ethyl acetate (300 ml) is added to the reaction solution, which is then subjected to filtration using celite. The resulting filtrate is poured into water. The organic phase is washed with a saturated sodium bicarbonate aqueous solution, dried using magnesium sulfate and then concentrated under reduced pressure. The concentrated residue is purified by silica gel column chromatography (developing solvent: ethyl acetate/hexane=1/30) to obtain a compound 24b (7.9 g).

(Synthesis of Compound (24c))

A sodium nitrite (1.5 g) aqueous solution (15 ml) is added dropwise to a solution mixture of chloroform (110 ml) and acetic acid (150 ml) containing the compound 24b (7.9 g) at 10° C. After the mixture is stirred for one hour, the reaction solution is poured into a chloroform/sodium bicarbonate aqueous solution and the organic phase is washed with saturated brine. The organic phase is then purified by silica gel column chromatography (developing solvent: ethyl acetate/hexane=1/3) to obtain a compound 24c (5.8 g).

(Synthesis of Compound (24d))

10 wt % Pd/C (0.4 g) is added as a catalyst to a solution mixture of methanol (25 ml) and tetrahydrofuran (30 ml) containing the compound 24c (5.8 g). The mixture is stirred at room temperature for 24 hours in a atmospheric pressure hydrogen atmosphere. After the catalyst is removed, an ethanol solution of 1,5-naphthalenedisulfonic acid tetrahydrate (4.2 g) was added to the solution, which is then concentrated under reduced pressure. The precipitated crystals are washed with acetonitrile to thereby obtain 1,5-naphthalene disulfonate of a compound 24d (6.0 g).

(Synthesis of the Exemplified Compound (24))

An aqueous solution (100 ml) containing ammonium persulfate (3.2 g) and sodium carbonate (3.7 g) is added dropwise to a solution mixture of ethanol (200 ml) and THF (200 ml) containing the compound 8a (1 g) and the 1,5-naphthalenedisulfonate of the compound 24d (3.6 g) at 10° C., and the mixture is stirred for one hour. The reaction solution is poured into chloroform/1N hydrochloric acid aqueous solution. The organic phase is dried by magnesium sulfate and then concentrated under reduced pressure. The concentrated residue is purified by silica gel column chromatography (developing solvent: chloroform/methanol=80/1) to thereby obtain the exemplified compound 24 (1.75 g). The compound is identified by the elemental analysis and the measurement of NMR and MASS spectrum.

$^1$H-NMR (CDCl$_3$)

δ: 0.78 (6H, m), 0.93 (3H, t), 0.98-1.56 (25H, m), 2.59 (2H, t), 3.15 (4H, m), 5.89 (1H, s), 6.20 (1H, s), 6.43 (1H, s), 7.16 (2H, d), 7.50 (2H, d), 7.58 (2H, d), 7.67-7.77 (6H, m), 8.71 (1H, s), 12.06 (1H, s)

λmax=624.5 nm, ε=102000 (CHCl$_3$ solution)

The dichroic dyes used for the liquid crystal element of the present invention may be used either singly or mixing two or more. When plural dyes are mixed, the dyes of the present invention may be mixed among them or the dye of the present invention may be mixed with known dichroic dyes. Examples of these known dyes include those described in, for example, A. V. Ivashchenko, Diachronic Dyes for Liquid Crystal Display, CRC, 1994. For display of a black color, it is necessary to absorb light in the entire visible region and it is preferable to mix plural dichroic dyes.

Any liquid crystal may be used as the host liquid crystal used for the liquid crystal element of the present invention insofar as it can coexist with the aforementioned dichroic dyes and, for example, liquid crystal compounds exhibiting a nematic phase or smectic phase may be utilized. Specific examples of these liquid crystal compounds include azomethine compounds, cyanobiphenyl compounds, cyanophenyl esters, fluorine-substituted phenyl esters, cyclohexanecarboxylic acid phenyl esters, fluorine-substituted cyclohexanecarboxylic acid phenyl esters, cyanophenylcyclohexane, fluorine-substituted phenylcyclohexane, cyano-substituted phenylpyrimidine, fluorine-substituted phenylpyrimidine, alkoxy-substituted phenylpyrimidine, fluorine-substituted alkoxy-substituted phenylpyrimidine, phenyldioxane, tolane type compounds, fluorine-substituted tolane compounds and alkenylcyclohexylbenzonitrile. The host liquid crystal is described in detail in "Liquid Crystal Device Handbook" edited by the Japan Society for the Promotion of Science, No. 142 Committee, the Nikkan Kogyo Shimbun, Ltd. (1989), pp. 154-192 and pp. 715-722. Host liquid crystals which are suitable to TFT drive and substituted with fluorine may also be used.

A compound exhibiting no liquid crystallinity may be compounded in the liquid crystal composition of the present invention for the purpose of changing the properties (e.g., the temperature range of a liquid crystal phase) of the host liquid crystal. The liquid crystal composition of the present invention may contain compounds such as a chiral compound, ultraviolet absorber and antioxidant. Examples of such an additive include chiral agents for TN or STN described in "Liquid Crystal Device Handbook" edited by the Japan Society for the Promotion of Science, No. 142 Committee, the Nikkan Kogyo Shimbun, Ltd. (1989), pp. 199-202.

The ratio of the dichroic dye to the host liquid crystal in the liquid crystal composition of the present invention is preferably 0.1 to 15% by mass and particularly preferably 0.5 to 6% by mass though any ratio is allowed.

The dissolution of the dichroic dye in the host liquid crystal can be accomplished by utilizing mechanical agitation, heating, ultrasonic wave or combinations of these means.

The liquid crystal element of the present invention may be sandwiched between paired electrode substrates to make a product. As the electrode substrate to be used for the liquid crystal element of the present invention, a glass or plastic substrate is usually used. Examples of materials of the plastic substrate include acrylic resins, polycarbonate resins and epoxy resins. The substrate is described in detail in "Liquid Crystal Device Handbook" edited by the Japan Society for the Promotion of Science, No. 142 Committee, the Nikkan Kogyo Shimbun, Ltd. (1989), pp. 218-231. An electrode layer, preferably a transparent electrode, is formed on the substrate. As the electrode layer, indium oxide, indiumtin oxide (ITO) or tin oxide is used. For the transparent electrode, those described in "Liquid Crystal Device Handbook" edited by the Japan Society for the Promotion of Science, No. 142 Committee, the Nikkan Kogyo Shimbun, Ltd. (1989), pp. 232-239 may be used.

In the liquid crystal element of the present invention, it is preferable to form a layer the surfaces of which are in contact with the liquid crystal and the substrate and have been subjected to orientation treatment. Examples of the orientation treatment include a method of orientating by applying quaternary ammonium salt, a method of orientating by applying a polyimide and by carrying out rubbing treatment, a method of orientating by vapor-depositing $SiO_x$ from a slant direction and a method of orientating by irradiation with light making use of photoisomerization. As the orientation film, those described in "Liquid Crystal Device Handbook" edited by the Japan Society for the Promotion of Science, No. 142 Committee, the Nikkan Kogyo Shimbun, Ltd. (1989), pp. 240-256 may be used.

The liquid crystal element of the present invention may be injected into a 1 to 50-μm-wide space formed between the substrates through a spacer. As the spacer, those described in "Liquid Crystal Device Handbook" edited by the Japan Society for the Promotion of Science, No. 142 Committee, the Nikkan Kogyo Shimbun, Ltd. (1989), pp. 257-262 may be used.

The liquid crystal element of the present invention may be driven by a simple matrix drive system or an active matrix drive system using a thin layer transistor (TFT). As the drive system, those described in "Liquid Crystal Device Handbook" edited by the Japan Society for the Promotion of Science, No. 142 Committee, the Nikkan Kogyo Shimbun, Ltd. (1989), pp. 387-460 may be used.

Examples of the liquid crystal display using the liquid crystal element of the present invention include, though it may be any system, (1) homogeneous orientation and (2) homeotropic orientation, (3) focal conic orientation and (4) homeotropic orientation as White-Taylor types (phase transition), (5) a combination with super twisted nematic (STN) and (6) a combination with a ferroelectric liquid crystal (FLC) described as the guest host system in "Liquid Crystal Device Handbook" edited by the Japan Society for the Promotion of Science, No. 142 Committee, the Nikkan Kogyo Shimbun, Ltd. (1989), p. 309, and (1) a Heilmeier type GH mode, (2) ¼ wavelength constant type GH mode, (3) double-layer type GH mode, (4) phase transition type GH mode and (5) polymer dispersion liquid crystal (PDLC) type GH mode as described in Reflection Type Color LCD General Technologies, compiled under the supervision of Tatsuo Uchida, CMC Publishing Co., Ltd. (1999), Chapter 2-1 (GH Mode Reflection type Color LCD).

Moreover, the liquid crystal element of the present invention may be used in a laminate type GH mode as described in, for example, JP-A Nos. 10-67990, 10-239702, 10-133223, 10-339881, 11-52411, 11-64880 and 2000-221538 and in a GH mode using a microcapsule as described in, for example, JP-A No. 11-24090. The liquid crystal element of the present invention may also be used in reflection type liquid crystal displays as described in, for example, JP-A Nos. 6-235931, 6-235940, 6-265859, 7-56174, 9-146124, 9-197388, 10-20346, 10-31207, 10-31216, 10-31231, 10-31232, 10-31233, 10-31234, 10-82986, 10-90674, 10-111513, 10-111523, 10-123509, 10-123510, 10-206851, 10-253993, 10-268300, 11-149252 and 2000-2874. The liquid crystal element of the present invention may also be used in a polymer dispersion liquid crystal type GH mode as described in JP-A Nos. 5-61025, 5-265053, 6-3691, 6-23061, 5-203940, 6-242423, 6-289376, 8-278490 and 9-813174.

EXAMPLES

The present invention will be hereinafter explained in detail by way of examples, which, however, are not intended to be limiting of the present inventions.

Example 1

Any one of a comparative dye A-1 and the compounds 1, 8, 21 and 24 according to the present invention was dissolved in chloroform, and the sample solution was then placed in a 1-cm-thick quarts cell, to measure visible absorption spectrum by using an ultraviolet visible spectrophotometer. The results of measurement are shown in Table 1.

TABLE 1

| Sample | Compound | Absorption coefficient | Half value width | Remarks |
|---|---|---|---|---|
| 101 | A-1 | $2.6 \times 10^4$ | 120 nm | Comparative Example |
| 102 | 1 | $9.5 \times 10^4$ | 47 nm | Invention |
| 103 | 8 | $1.2 \times 10^5$ | 45 nm | Invention |
| 104 | 21 | $1.0 \times 10^5$ | 64 nm | Invention |
| 105 | 24 | $1.0 \times 10^5$ | 63 nm | Invention |

Comparative compound (A-1)

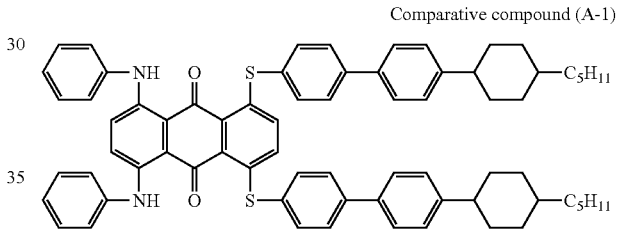

Compound 3-2 described in JP-A No. 2003-138262

As is clear from Table 1, the compound according to the present on has a high absorption coefficient and a narrow half value width, namely, a sharp hue.

Example 2

1.0 mg of each compound shown in Table 2 was dissolved in 100 mg of ZLI-1132 (trade name, manufactured by E. Merck) to prepare a liquid crystal composition. This liquid crystal composition was injected into a liquid crystal cell (equipped with an ITO transparent electrode, Polyimide orientation film+Rubbing treatment+Parallel arrangement, glass plate: 0.7 mm, cell gap: 8 μm, equipped with an epoxy resin seal, manufactured by E.H.C.) to manufacture an evaluation cell. This cell was irradiated with polarized light parallel to the direction of rubbing and polarized light perpendicular to the direction of rubbing to measure absorption spectrums (A∥ and A⊥) respectively by an ultraviolet visible spectrophotometer (UV2400PC) manufactured by Shimadzu Corporation. The order parameter S was calculated according to the following equation from these spectrums A∥ and A⊥ at each maximum absorption wavelength.

$$S=(A\|-A\perp)/(A\|+2 \cdot A\perp) \qquad \text{Equation 1}$$

The results of measurement are shown in Table 2. Here, the absorbance shows the absorption A∥ when polarized light parallel to the direction of rubbing is applied.

TABLE 2

| Compound | Maximum absorption wavelength | Absorbance | Order parameter S | Remarks |
|---|---|---|---|---|
| 1 | 632 nm | 0.76 | 0.71 | Invention |
| 8 | 639 nm | 2.40 | 0.72 | Invention |
| 13 | 643 nm | 1.77 | 0.75 | Invention |
| 15 | 639 nm | 1.02 | 0.78 | Invention |
| 21 | 639 nm | 2.12 | 0.85 | Invention |
| 23 | 642 nm | 1.77 | 0.80 | Invention |
| 24 | 639 nm | 1.58 | 0.81 | Invention |
| 25 | 639 nm | 2.48 | 0.84 | Invention |

It is understood clearly from Table 2 that the liquid crystal composition of the present invention imparts high absorbance and order parameter.

Example 3

1 mg of each compound shown in Table 3 was dissolved in 100 mg of a commercially available liquid crystal (trade name: "ZLI-5081", manufactured by E. Merck) to measure the order parameter S in the same manner as in Example 2. The results of measurement are shown in Table 3. Here, the absorbance indicates the absorption A∥ when polarized light parallel to the direction of rubbing is applied.

TABLE 3

| Compound | Maximum absorption wavelength | Absorbance | Order parameter S | Remarks |
|---|---|---|---|---|
| 8 | 632 nm | 1.20 | 0.76 | Invention |
| 21 | 629 nm | 1.82 | 0.84 | Invention |
| 23 | 633 nm | 0.78 | 0.82 | Invention |
| 24 | 628 nm | 0.82 | 0.80 | Invention |

It is understood clearly from Table 3 that the liquid crystal composition of the present invention imparts high order parameter even if a fluorine type host liquid crystal is used.

Example 4

(1) Production of Liquid Crystal Cell

A polyimide orientation film "JALS-682-R3" manufactured by JSR Corporation was applied to the surface of a glass substrate on which ITO was vapor-deposited, and then baked at 180° C. After the substrate was subjected to rubbing treatment (parallel orientation), it was processed using a spacer (6.5 μm) manufactured by Catalysts & Chemicals Industries Co., Ltd. and an epoxy adhesive to manufacture a sandwich type liquid crystal cell. The pre-tilt angle of the orientation of the liquid crystal on the orientation film was 88°.

(2) Production of Liquid Crystal Element 1 mg of each of the compounds shown in Table 4 was mixed with 100 mg of a fluorine type liquid crystal (trade name: "MLC-6609", manufactured by E. Merck) having negative dielectric constant anisotropy and the mixture was stirred under heating at 80° C. The mixture was cooled to room temperature and injected into the cell produced in (1) to manufacture a liquid crystal element.

(3) Measurement of Absorption Spectrum when Voltage is Applied

Each produced liquid crystal element was irradiated with polarized light parallel to the direction of rubbing to measure absorption spectrums (A∥(0 V)) by UV3100 (ultraviolet visible spectrophotometer, manufactured by Shimadzu Corporation). Next, rectangular a.c. voltage (10 V, 60 Hz) was applied to each produced liquid crystal element, which was then irradiated with polarized light parallel to the direction of rubbing to measure each absorption spectrum (A∥(10 V)). Dmax/Dmin was calculated from the measured values of (A∥(0 V)) and (A∥(10 V)) at each maximum absorption wavelength according to the following equation. The results are shown in Table 4.

Dmax/Dmin={A∥(10 V)}/{A∥(0 V)}

TABLE 4

| Compound | Dmax/Dmin | Remarks |
|---|---|---|
| 21 | 15 | Invention |
| 23 | 14 | Invention |
| 24 | 13 | Invention |

It is understood clearly from Table 4 that the liquid crystal element of the present invention imparts a high concentration ratio Dmax/Dmin even if a fluorine type host liquid crystal having negative dielectric constant anisotropy is used.

What is claimed is:

1. A liquid crystal composition, comprising a compound represented by the following formula (2):

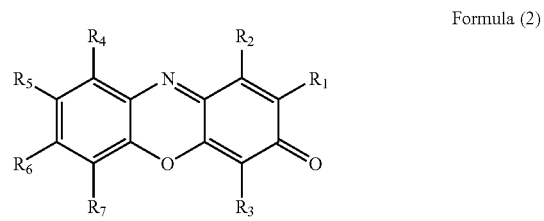

Formula (2)

wherein $R_1$, $R_2$, $R_3$, $R_4$, $R_5$, $R_6$ and $R_7$ each independently represent a hydrogen atom or a substituent; and $R_1$ and $R_2$ are not combined with each other to form a ring.

2. A liquid crystal composition of claim 1, wherein in the compound represented by the formula (2), $R_1$ is a halogen atom, a carbamoyl group, an acylamino group, an acyl group, an aryloxycarbonyl group or an alkoxycarbonyl group; and $R_6$ is an amino group, a hydroxyl group, a mercapto group, an alkylthio group, an arylthio group, an alkoxy group or an aryloxy group.

3. A liquid crystal composition of claim 1, wherein the compound represented by the formula (2) has a substituent represented by the following formula (3):

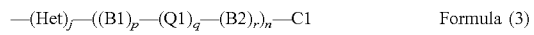

Formula (3)

wherein Het represents an oxygen atom or a sulfur atom; B1 and B2 each independently represent a divalent aryl group; a heteroaryl group or a cyclic aliphatic hydrocarbon group; Q1 represents a divalent connecting group; C1 represents an alkyl group, a cycloalkyl group, an alkoxy group, an alkoxycarbonyl group or an acyloxy group; j denotes 0 or 1; p, q and r each independently denote an integer from 0 to 5; and n denotes an integer from 1 to 3, provided that (p+r)×n is a number of 3 or more and 10 or less.

4. A liquid crystal element comprising a pair of electrodes at least one of which is a transparent electrode and a liquid crystal layer disposed between the pair of electrodes wherein the liquid crystal layer contains the liquid crystal composition comprising a compound represented by the following formula (1) and a liquid crystal:

Formula (1)

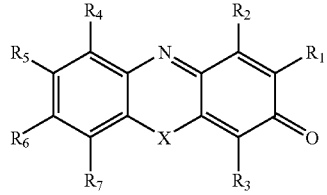

wherein $R_1$, $R_2$, $R_3$, $R_4$, $R_5$, $R_6$ and $R_7$ each independently represent a hydrogen atom or a substituent; X represents an oxygen atom or a sulfur atom; and $R_1$ and $R_2$ are not combined with each other to form a ring.

5. A liquid crystal element of claim 4, wherein the compound contained in the liquid crystal composition and represented by the formula (1) is a compound represented by the following formula (2):

Formula (2)

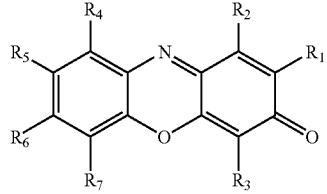

wherein $R_1$, $R_2$, $R_3$, $R_4$, $R_5$, $R_6$ and $R_7$ each independently represent a hydrogen atom or a substituent.

6. A liquid crystal element of claim 5, wherein in the compound represented by the formula (2), $R_1$ is a halogen atom, a carbamoyl group, an acylamino group; an acyl group, an aryloxycarbonyl group or an alkoxycarbonyl group and $R_6$ is an amino group, a hydroxyl group, a mercapto group, an alkylthio group, an arylthio group, an alkoxy group or an aryloxy group.

7. A liquid crystal element of claim 5, wherein the compound represented by the formula (2) has a substituent represented by the following formula (3):

—(Het)$_j$—((B1)$_p$—(Q1)$_q$—(B2)$_r$)$_n$—C1    Formula (3)

wherein Het represents an oxygen atom or a sulfur atom; B1 and B2 each independently represent a divalent aryl group, a heteroaryl group or a cyclic aliphatic hydrocarbon group; Q1 represents a divalent connecting group; C1 represents an alkyl group, a cycloalkyl group, an alkoxy group, an alkoxycarbonyl group or an acyloxy group; j denotes 0 or 1, p, q and r each independently denote an integer from 0 to 5; and n denotes an integer from 1 to 3, provided that (p+r)×n is a number of 3 or more and 10 or less.

8. A compound represented by the following formula (4):

Formula (4)

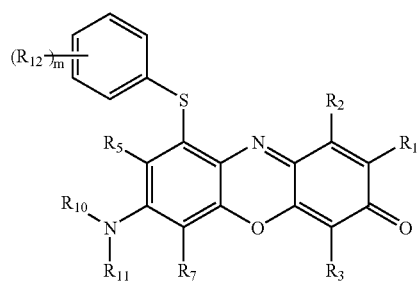

wherein $R_1$, $R_2$, $R_3$, $R_5$ and $R_7$ each independently represent a hydrogen atom or a substituent; $R_{10}$ and $R_{11}$ each independently represent a hydrogen atom, an alkyl group or an aryl group; $R_{12}$ represents a substituent; and m denotes an integer from 0 to 5.

9. A liquid crystal composition comprising the compound represented by the following formula (4):

Formula (4)

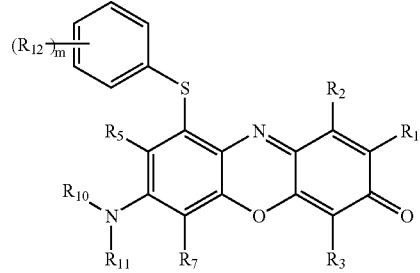

wherein $R_1$, $R_2$, $R_3$, $R_5$ and $R_7$ each independently represent a hydrogen atom or a substituent; $R_{10}$ and $R_{11}$ each independently represent a hydrogen atom, an alkyl group or an aryl group; $R_{12}$ represents a substituent; and m denotes an integer from 0 to 5.

10. A liquid crystal element comprising a pair of electrodes at least one of which is a transparent electrode and a liquid crystal layer disposed between the pair of electrodes wherein the liquid crystal layer contains the liquid crystal composition comprising a compound represented by the following formula (4):

Formula (4)

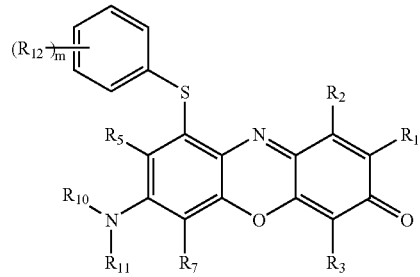

wherein $R_1$, $R_2$, $R_3$, $R_5$ and $R_7$ each independently represent a hydrogen atom or a substituent; $R_{10}$ and $R_{11}$ each independently represent a hydrogen atom, an alkyl group or an aryl group; $R_{12}$ represents a substituent; and m denotes an integer from 0 to 5.

11. A liquid crystal composition of claim 1, wherein $R_6$ is the amino group, and wherein the amino group is an alkylamino group or an arylamino group.

12. The liquid crystal element of claim 6, wherein $R_6$ is the amino group, and wherein the amino group is an alkylamino group or an arylamino group.

13. The liquid crystal composition of claim 1, wherein $R_1$ is a halogen atom, a carbamoyl group, an acylamino group, an acyl group, an aryloxycarbonyl group or an alkoxycarbonyl group.

* * * * *